US011647940B2

United States Patent
Badie et al.

(10) Patent No.: US 11,647,940 B2
(45) Date of Patent: May 16, 2023

(54) R-R INTERVAL PATTERN RECOGNITION FOR USE IN ARRHYTHMIA DISCRIMINATION

(71) Applicant: Pacesetter, Inc., Sylmar, CA (US)

(72) Inventors: Nima Badie, Berkeley, CA (US); Fujian Qu, San Jose, CA (US); Jong Gill, Valencia, CA (US)

(73) Assignee: Pacesetter, Inc, Sylmar, CA (US)

( * ) Notice: Subject to any disclaimer, the term of this patent is extended or adjusted under 35 U.S.C. 154(b) by 183 days.

(21) Appl. No.: 17/226,915

(22) Filed: Apr. 9, 2021

(65) Prior Publication Data

US 2021/0338136 A1 Nov. 4, 2021

Related U.S. Application Data

(60) Provisional application No. 63/019,550, filed on May 4, 2020.

(51) Int. Cl.
*A61B 5/352* (2021.01)
*A61B 5/361* (2021.01)
(Continued)

(52) U.S. Cl.
CPC .............. *A61B 5/352* (2021.01); *A61B 5/361* (2021.01); *A61B 5/363* (2021.01); *A61N 1/3704* (2013.01); *A61N 1/3956* (2013.01)

(58) Field of Classification Search
CPC ......... A61B 5/352; A61B 5/361; A61B 5/363; A61B 5/686; A61N 1/3704; A61N 1/3956;
(Continued)

(56) References Cited

U.S. PATENT DOCUMENTS 6,347,245 B1 * 2/2002 Lee .................. A61B 5/7203
600/509
7,218,966 B2 5/2007 Haefner
(Continued)

FOREIGN PATENT DOCUMENTS

EP 1615693 B1 1/2011
EP 2079520 B1 11/2013
(Continued)

OTHER PUBLICATIONS

Extended European Search Report dated Sep. 29, 2021, European Patent Application No. 21168038.4-1132.
(Continued)

*Primary Examiner* — Catherine M Voorhees
(74) *Attorney, Agent, or Firm* — Vierra Magen Marcus LLP

(57) ABSTRACT

Described herein are methods, devices, and systems that improve arrhythmia episode detection specificity, such as, but not limited to, atrial fibrillation (AF) episode detection specificity. Such a method can include obtaining an ordered list of R-R intervals within a window leading up to a detection of a potential arrhythmia episode, determining a measure of a dominant repeated R-R interval pattern within the window, and comparing the measure of the dominant repeated R-R interval pattern to a pattern threshold. If the measure of the dominant repeated R-R interval pattern is below the pattern threshold, that is indicative of a regularly irregular pattern being present, and there is a determination that the detection of the potential arrhythmia episode does not correspond to an actual arrhythmia episode. Such embodiments can beneficially be used to significantly reduce the number of false positive arrhythmia detections.

20 Claims, 8 Drawing Sheets

(51) Int. Cl.
*A61B 5/363* (2021.01)
*A61N 1/37* (2006.01)
*A61N 1/39* (2006.01)

(58) Field of Classification Search
CPC .. A61N 1/3621; A61N 1/3624; A61N 1/3925; A61N 1/362; A61N 1/36507; A61N 1/395; A61N 1/3962
See application file for complete search history.

(56) References Cited

U.S. PATENT DOCUMENTS

| | | | |
|---|---|---|---|
| 7,266,409 B2 | 9/2007 | Gunderson | |
| 7,283,863 B2 | 10/2007 | Gunderson et al. | |
| 7,333,855 B2 | 2/2008 | Gunderson et al. | |
| 7,404,799 B1* | 7/2008 | Koh | A61N 1/365 607/18 |
| 7,412,282 B2 | 8/2008 | Houben | |
| 7,537,569 B2 | 5/2009 | Sarkar et al. | |
| 7,582,061 B2 | 9/2009 | Li et al. | |
| 7,623,911 B2 | 11/2009 | Sarkar et al. | |
| 7,630,756 B2 | 12/2009 | Linker | |
| 7,634,310 B2 | 12/2009 | Lee et al. | |
| 7,774,049 B2 | 8/2010 | Ghanem et al. | |
| 7,774,062 B2 | 8/2010 | Kim et al. | |
| 7,783,354 B2 | 8/2010 | Gunderson | |
| 7,818,056 B2 | 10/2010 | Kim et al. | |
| 7,831,301 B2 | 11/2010 | Cao et al. | |
| 7,894,893 B2* | 2/2011 | Kim | A61B 5/35 600/515 |
| 7,912,545 B2 | 3/2011 | Li et al. | |
| 8,078,277 B2 | 12/2011 | Gunderson et al. | |
| 8,160,686 B2 | 4/2012 | Allavatam et al. | |
| 8,265,737 B2 | 9/2012 | Warren et al. | |
| 8,406,872 B2 | 3/2013 | Stadler et al. | |
| 8,437,840 B2 | 5/2013 | Patel et al. | |
| 8,437,851 B2 | 5/2013 | Corbucci et al. | |
| 8,473,042 B2 | 6/2013 | McCarthy et al. | |
| 8,506,500 B2 | 8/2013 | Li et al. | |
| 8,521,281 B2 | 8/2013 | Patel et al. | |
| 8,560,058 B2 | 10/2013 | Babaeizadeh et al. | |
| 8,560,069 B2 | 10/2013 | Zhang | |
| 8,577,455 B2 | 11/2013 | Mitrani et al. | |
| 8,583,221 B1 | 11/2013 | Patel et al. | |
| 8,588,895 B2 | 11/2013 | Sanghera et al. | |
| 8,588,896 B2 | 11/2013 | Allavatam et al. | |
| 8,626,280 B2 | 1/2014 | Allavatam et al. | |
| 8,639,316 B2 | 1/2014 | Sarkar | |
| 8,744,559 B2 | 6/2014 | Houben et al. | |
| 8,750,994 B2 | 6/2014 | Ghosh et al. | |
| 8,774,909 B2 | 7/2014 | Patel et al. | |
| 8,781,585 B2 | 7/2014 | Gunderson et al. | |
| 8,792,971 B2 | 7/2014 | Gunderson et al. | |
| 8,886,296 B2 | 11/2014 | Patel | |
| 8,897,863 B2 | 11/2014 | Linker | |
| 8,914,106 B2 | 12/2014 | Charlton et al. | |
| 8,942,793 B2 | 1/2015 | Eberle et al. | |
| 9,101,278 B2 | 8/2015 | Fischell et al. | |
| 9,167,747 B1 | 10/2015 | Andros et al. | |
| 9,307,920 B2 | 4/2016 | Mahajan et al. | |
| 9,314,210 B2 | 4/2016 | Li | |
| 9,339,662 B2 | 5/2016 | Allavatam et al. | |
| 9,381,370 B2 | 7/2016 | Gunderson | |
| 9,675,261 B2 | 6/2017 | Cao et al. | |
| 9,682,238 B2 | 6/2017 | Zhang et al. | |
| 9,724,007 B2 | 8/2017 | Cole | |
| 9,962,100 B2 | 5/2018 | Allavatam et al. | |
| 9,993,653 B2 | 6/2018 | Bardy et al. | |
| 9,999,368 B2 | 6/2018 | Perschbacher et al. | |
| 10,004,418 B2 | 6/2018 | Cao et al. | |
| 10,183,171 B2 | 1/2019 | Ostroff et al. | |
| 10,194,816 B2 | 2/2019 | Perschbacher et al. | |
| 10,413,207 B2 | 9/2019 | Sarkar et al. | |
| 10,576,288 B2 | 3/2020 | Cao et al. | |
| 10,582,870 B2 | 3/2020 | Allavatam et al. | |
| 10,702,180 B2 | 7/2020 | Perschbacher et al. | |
| 10,709,379 B2 | 7/2020 | Warren et al. | |
| 2003/0144700 A1 | 7/2003 | Brown et al. | |
| 2006/0247548 A1* | 11/2006 | Sarkar | A61B 5/363 600/515 |
| 2007/0288060 A1* | 12/2007 | Stickney | A61B 5/024 600/301 |
| 2013/0030307 A1* | 1/2013 | Rajan | A61B 5/0024 600/479 |
| 2015/0141860 A1* | 5/2015 | Linker | A61B 5/361 600/518 |
| 2017/0135593 A1 | 5/2017 | Huang et al. | |

FOREIGN PATENT DOCUMENTS

| | | |
|---|---|---|
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3592419 B1 | 1/2020 |
| EP | 2741662 B1 | 3/2021 |
| WO | WO2021/154578 A1 | 8/2021 |

OTHER PUBLICATIONS

Response to Extended European Search Report dated Nov. 15, 2021, European Patent Application No. 21168038.4-1132.

* cited by examiner

| Interval Number | R-R Interval (ms) |
|---|---|
| 1 | 734.4 |
| 2 | 632.8 |
| 3 | 921.9 |
| 4 | 773.4 |
| 5 | 617.2 |
| 6 | 1039.1 |
| 7 | 773.4 |
| 8 | 625.0 |
| 9 | 1007.8 |
| 10 | 757.8 |
| 11 | 632.8 |
| 12 | 937.5 |
| 13 | 757.8 |
| 14 | 632.8 |
| 15 | 1000.0 |
| 16 | 765.6 |
| 17 | 625.0 |
| 18 | 710.9 |
| 19 | 273.4 |
| 20 | 742.2 |
| 21 | 625.0 |
| 22 | 937.5 |
| 23 | 742.2 |
| 24 | 617.2 |
| 25 | 789.1 |
| 26 | 257.8 | ← Minimum
| 27 | 695.3 |
| 28 | 625.0 |
| 29 | 890.6 |
| 30 | 757.8 |
| 31 | 617.2 |
| 32 | 992.2 |
| 33 | 750.0 |
| 34 | 625.0 |
| 35 | 1015.6 |
| 36 | 765.6 |
| 37 | 632.8 |
| 38 | 1085.9 | ← Maximum
| 39 | 820.3 |
| 40 | 625.0 |

*FIG. 2*

R-R INTERVAL PATTERN RECOGNITION FOR USE IN ARRHYTHMIA DISCRIMINATION

PRIORITY CLAIM

This application claims priority to U.S. Provisional Patent Application No. 63/019,550, filed May 4, 2020, which is incorporated herein by reference.

FIELD OF TECHNOLOGY

Embodiments described herein generally relate to methods, systems, and devices for performing arrhythmia discrimination, and more particularly, for improving arrhythmia episode detection specificity, such as, but not limited to, atrial fibrillation (AF) episode detection specificity.

BACKGROUND

Various types of implantable medical devices (IMDs) are used to monitor for cardiac arrhythmias. Some types of IMDs, such as implantable cardiac pacemakers and implantable cardiac defibrillators (ICDs), are capable of providing appropriate therapy in response to detected cardiac arrhythmias. Other types of IMDs, such as insertable cardiac monitors (ICMs), are used for diagnostic purposes. ICMs have been increasingly used to diagnose cardiac arrhythmias, such as atrial fibrillation (AF).

Atrial Fibrillation (AF) is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions).

There are a few ICMs that are commercially available, including the Confirm Rx™ ICM, manufactured by Abbott Laboratories, of Chicago, Ill., the Reveal LINQ™ ICM, manufactured by Medtronic, Inc., of Minneapolis, Minn., and the BioMonitor™ 2 (AF and S versions), manufactured by Biotronik SE & Co. KG, of Berlin, Germany. When an ICM detects an episode of an arrhythmia, such as AF, information about the episode may be recorded and a corresponding EGM segment (and/or other information) can be transmitted from the ICM to a patient care network for clinician review. False positive arrhythmia detections are highly undesirable, as the burden of sorting through large numbers of clinically irrelevant episodes of arrhythmia can be time consuming and costly. Further, false positive arrhythmia detections may cause additional expense for technician review, patients may suffer unnecessary anxiety, and the false positive arrhythmia detections may result in expensive, uncomfortable, and inconvenient follow-on testing.

One source of false positive arrhythmia detections, such as false positive AF detections, results from regularly irregular "patterns" of R-R intervals. For example, multiple atrial foci of activity can take turns activating the ventricles. While this may result in high heart rate variability (i.e., R-R interval variability) and trigger AF detection, the heart rate patterns repeat themselves. This phenomenon is not the "irregularly irregular" chaotic rhythm attributed to true AF, and these episodes should be rejected. However, current IMDs, such as ICMs, typically trigger false positive AF detects from these regularly irregular "patterns" of R-R intervals. Accordingly, there is a still a need for improved techniques for distinguishing such patterns from actual chaotic rhythms resulting from AF, and more generally, for performing improved arrhythmia discrimination.

A heartbeat rhythm may be (i) regular, (ii) regularly irregular, or (iii) irregularly irregular. An irregularly irregular rhythm exhibits no pattern to the heartbeat intervals and is typically associated with AF. In contrast, a regularly irregular rhythm that exhibits an underlying or hidden pattern, which may not be apparent using conventional automated AF detection methods, is typically not associated with AF, but may lead to false positive AF detections. In particular, a healthy heart rhythm that is found to be regularly irregular is not likely associated with AF.

Automated methods for detecting AF episodes that rely on detecting irregularity in sequential heartbeat intervals (e.g., R-R intervals) to determine the likelihood that the rhythm is AF can be fooled by regularly irregular pattern in a heartbeat signal. This can lead to the automated method falsely identifying AF, i.e., to a false positive AF detection.

SUMMARY

Certain embodiments of the present technology are directed to methods, devices, and systems that can be used to improve arrhythmia episode detection specificity, such as, but not limited to, AF episode detection specificity.

In accordance with certain embodiments, a method for improving arrhythmia episode detection specificity comprises obtaining an ordered list of R-R intervals within a window leading up to a detection of a potential arrhythmia episode (wherein each of the R-R intervals has a respective duration), and determining (based on the ordered list) a measure of a dominant repeated R-R interval pattern within the window. The method additional includes comparing the measure of the dominant repeated R-R interval pattern to a pattern threshold, and in response to the measure of the dominant repeated R-R interval pattern being below the pattern threshold, determining that the detection of the potential arrhythmia episode does not correspond to an actual arrhythmia episode.

In accordance with certain embodiments, the determining the measure of the dominant repeated R-R interval pattern within the window comprises: for each of k=1 to M, where M is an integer that is at least 4, determining an indicator of a median R-R interval difference between pairs of the R-R intervals within the window that are k intervals apart, to thereby produce M indicators of the median R-R interval difference; identifying a minimum of the M indicators of the median R-R interval difference; and determining the measure of the dominant repeated R-R interval pattern within the window as being the minimum of the M indicators of the median R-R interval difference.

In accordance with certain embodiments, the M indicators of the median R-R interval difference that are determined comprise M median percent difference values each of which is determined using the equation: Median Percent Difference for $k=\text{MEDIAN}(100*|RR(n)-RR(n+k)|/RR(n))$, for intervals $n=1:N$ and interval separations $k=1:M$, where $RR(n)$ is a $n^{th}$ R-R interval within the window, RR(n+k) is a $(n+k)^{th}$ R-R interval within the window, |RR(n)−RR(n+k)| is the absolute value of RR(n)−RR(n+k), and N is a total number of R-R intervals within the window.

In accordance with certain embodiments, the method is for use by an implantable medical device (IMD) that is configured to at least one of save within memory of the IMD or transmit to an external device, data corresponding one or more arrhythmia episodes detected by the IMD, so that the data is available at a later time for further analysis. The above summarized steps are performed by the IMD in response to the IMD detecting the potential arrhythmia episode. After the IMD determines that the detection of the arrhythmia episode does not correspond to an actual arrhythmia episode, the IMD at least one of allows data corresponding to the potential arrhythmia episode to be overwritten or prevents data corresponding to the potential arrhythmia episode from being transmitted to an external device.

In accordance with certain embodiments, the window comprises a specified period of time, and the obtaining the ordered list of R-R intervals comprises: obtaining an electrogram (EGM) or electrocardiogram (ECG) segment corresponding to the specified period of time leading up to the detection of the potential arrhythmia episode; identifying R-waves within the EGM or ECG segment; and determining intervals between consecutive ones of the R-waves.

Certain embodiments of the present technology are directed to a device comprising one or more electrodes, a sensing circuit, and at least one of a processor or controller. The sensing circuit is coupled to the one or more electrodes and configured to obtain a signal indicative of electrical activity of a patient's heart. The at least one of a processor or controller is configured to obtain an ordered list of R-R intervals within a window leading up to a detection of a potential arrhythmia episode, wherein each of the R-R intervals has a respective duration; determine (based on the ordered list of R-R intervals within the window) a measure of a dominant repeated R-R interval pattern within the window; and compare the measure of the dominant repeated R-R interval pattern to a pattern threshold. The at least one of a processor or controller is also configured to determine that the detection of the potential arrhythmia episode does not correspond to an actual arrhythmia episode, if the measure of the dominant repeated R-R interval pattern is below the pattern threshold. In accordance with certain embodiments, the at least one of a processor or controller is/are configured to determine the measure of the dominant repeated R-R interval pattern within the window by: determining an indicator of a median R-R interval difference between pairs of the R-R intervals within the window that are k intervals apart, for each of k=1 to M, where M is an integer that is at least 4, to thereby produce M indicators of the median R-R interval difference; and identifying a minimum of the M indicators of the median R-R interval difference; and determining the measure of the dominant repeated R-R interval pattern within the window as being the minimum of the M indicators of the median R-R interval difference.

In accordance with certain embodiments, the M indicators of the median R-R interval difference comprise M median percent difference values each of which is determined, by the at least one of a processor or controller, using the equation: Median Percent Difference for k=MEDIAN (100*|RR(n)−RR(n+k)|/RR(n)), for intervals n=1:N and interval separations k=1:M, where RR(n) is a $n^{th}$ R-R interval within the window, RR(n+k) is a $(n+k)^{th}$ R-R interval within the window, |RR(n)−RR(n+k)| is the absolute value of RR(n)−RR(n+k), and N is a total number of R-R intervals within the window.

In accordance with certain embodiments, the device comprises one of the following: a user wearable device; an insertable cardiac monitor (ICM); a cardiac pacemaker to which one or more leads is/are attached; a leadless cardiac pacemaker (LCP); or an implantable cardioverter defibrillator (ICD).

In accordance with certain embodiments, the device is an IMD and includes a transceiver configured to wireless communicate with an external device. Further, the IMD is configured to at least one of save within memory of the IMD or transmit to an external device, data corresponding one or more arrhythmia episodes detected by the IMD, so that the data is available at a later time for further analysis. In certain such embodiments, after the IMD determines that the detection of the arrhythmia episode does not correspond to an actual arrhythmia episode, the IMD allows data corresponding to the potential arrhythmia episode to be overwritten and/or prevents data corresponding to the potential arrhythmia episode from being transmitted to an external device using the transceiver.

In accordance with certain embodiments, a method for improving arrhythmia episode detection specificity comprises obtaining an ordered list of R-R intervals within a window leading up to a detection of a potential arrhythmia episode, wherein each of the R-R intervals has a respective duration. The method also includes, for a value for k, selected from a range of values for k, determining a corresponding indicator of a median R-R interval difference between pairs of the R-R intervals within the window that are k intervals apart; comparing the indicator of the median R-R interval difference to a threshold; and if the indicator of the median R-R interval difference is less than the threshold, then determining that the detection of the potential arrhythmia episode does not correspond to an actual arrhythmia episode. The method also includes, if the indicator of the median R-R interval difference is not less than the threshold, then repeating the aforementioned steps for another selected value of k, until there is a determination that the detection of the potential arrhythmia episode does not correspond to an actual arrhythmia episode, or until there are no additional values to select for k within the range of values for k. In accordance with certain embodiment, the range of values for k is from 1 to M, where M is an integer that is at least 4. In certain such embodiments, an initial value for k, that is selected from the range of values for k, is 1, and each time the aforementioned steps are repeated for another selected value of k, the other selected value of k is produced by incrementing k so that k=k+1. In accordance with other embodiments, an initial value for k, that is selected from the range of values for k, is M, and each time the aforementioned steps are repeated for another selected value of k, the other selected value of k is produced by decrementing k so that k=k−1. In accordance with certain embodiments, the corresponding indicator of the median R-R interval difference between pairs of the R-R intervals, determined for a value of k, comprises a median percent difference value determined using the equation: Median Percent Difference=MEDIAN(100*|RR(n)−RR(n+k)|/RR(n)), for intervals n=1:N, where RR(n) is a $n^{th}$ R-R interval within the window, RR(n+k) is a $(n+k)^{th}$ R-R interval within the window, |RR(n)−RR(n+k)| is the absolute value of RR(n)−RR(n+k), and N is a total number of R-R intervals within the window.

Certain embodiments of the present technology are directed to a device comprising one or more electrodes, a sensing circuit, and at least one of a processor or controller. The sensing circuit is coupled to the one or more electrodes and configured to obtain a signal indicative of electrical activity of a patient's heart. The at least one of a processor or controller is configured to obtain an ordered list of R-R intervals within a window leading up to a detection of a potential arrhythmia episode, wherein each of the R-R intervals has a respective duration. The at least one of a processor or controller is also configured to, for a value for k, selected from a range of values for k, determine a corresponding indicator of a median R-R interval difference between pairs of the R-R intervals within the window that are k intervals apart; compare the indicator of the median R-R interval difference to a threshold; and determine that the detection of the potential arrhythmia episode does not correspond to an actual arrhythmia episode, if the indicator of the median R-R interval difference is less than the threshold. In accordance with certain such embodiments, if for a value of k, the at least one of a processor or controller determines that the detection of the potential arrhythmia episode does not correspond to an actual arrhythmia episode, then an indicator of the median R-R interval is determined for one or more further values for k within the range of values, until there is a determination that the detection of the potential arrhythmia episode does not correspond to an actual arrhythmia episode, or until there are no additional values to select for k within the range of values for k. In accordance with certain such embodiments, the range of values for k is from 1 to M, where M is an integer that is at least 4, and wherein the at least one of a processor or controller are configured so that: an initial value for k, that is selected from the range of values for k, is 1, and each time there is another selected value of k, the other selected value of k is produced by incrementing k so that k=k+1; or an initial value for k, that is selected from the range of values for k, is M, and each time there is another selected value of k, the other selected value of k is produced by decrementing k so that k=k−1. In accordance with certain embodiments, the corresponding indicator of the median R-R interval difference between pairs of the R-R intervals, determined for a value of k, comprises a median percent difference value determined using the equation: Median Percent Difference=MEDIAN $(100*|RR(n)-RR(n+k)|/RR(n))$, for intervals n=1:N, where $RR(n)$ is a $n^{th}$ R-R interval within the window, $RR(n+k)$ is a $(n+k)^{th}$ R-R interval within the window, $|RR(n)-RR(n+k)|$ is the absolute value of $RR(n)-RR(n+k)$, and N is a total number of R-R intervals within the window.

In certain embodiments, pairwise differences between pairs of R-R intervals that are k intervals apart are represented as percentages, and the medians of N-k pairwise difference percentages are represented as a percentage, i.e., a median percent difference for k, as was summarized above. In other embodiments, pairwise differences between pairs of R-R intervals that are k intervals apart are represented as simple differences (i.e., $RR(n)-RR(n+k)$), aka deltas, that are not percentages, and the medians of N-k pairwise difference percentages are also represented as simple differences that are not percentages. In still other embodiments, pairwise differences between pairs of R-R intervals that are k intervals apart are represented as ratios, as are the medians thereof. For example, rather than determining the difference between the nth and $(n+k)^{th}$ R-R interval by calculating $RR(n)-RR(n+k)$, the difference can be represented by the ratio of $RR(n)/RR(n+k)$ or $RR(n+k)/RR(n)$, or by the higher of the two R-R intervals over the lower of the two R-R intervals being compared, or vice versa. The closer such a ratio is to unity (i.e., to one) the more likely a regular irregular pattern exists, which is an indicator of a non-arrhythmia event. Where ratios are used, the threshold used can be a threshold range, e.g., between 0.8 and 1.2, but not limited thereto. Other variations are also possible and within the scope of the embodiments described herein.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIG. 2 shows a table including a list of forty R-R intervals within the thirty-second window shown in FIG. 1.

DETAILED DESCRIPTION

Figure 1:
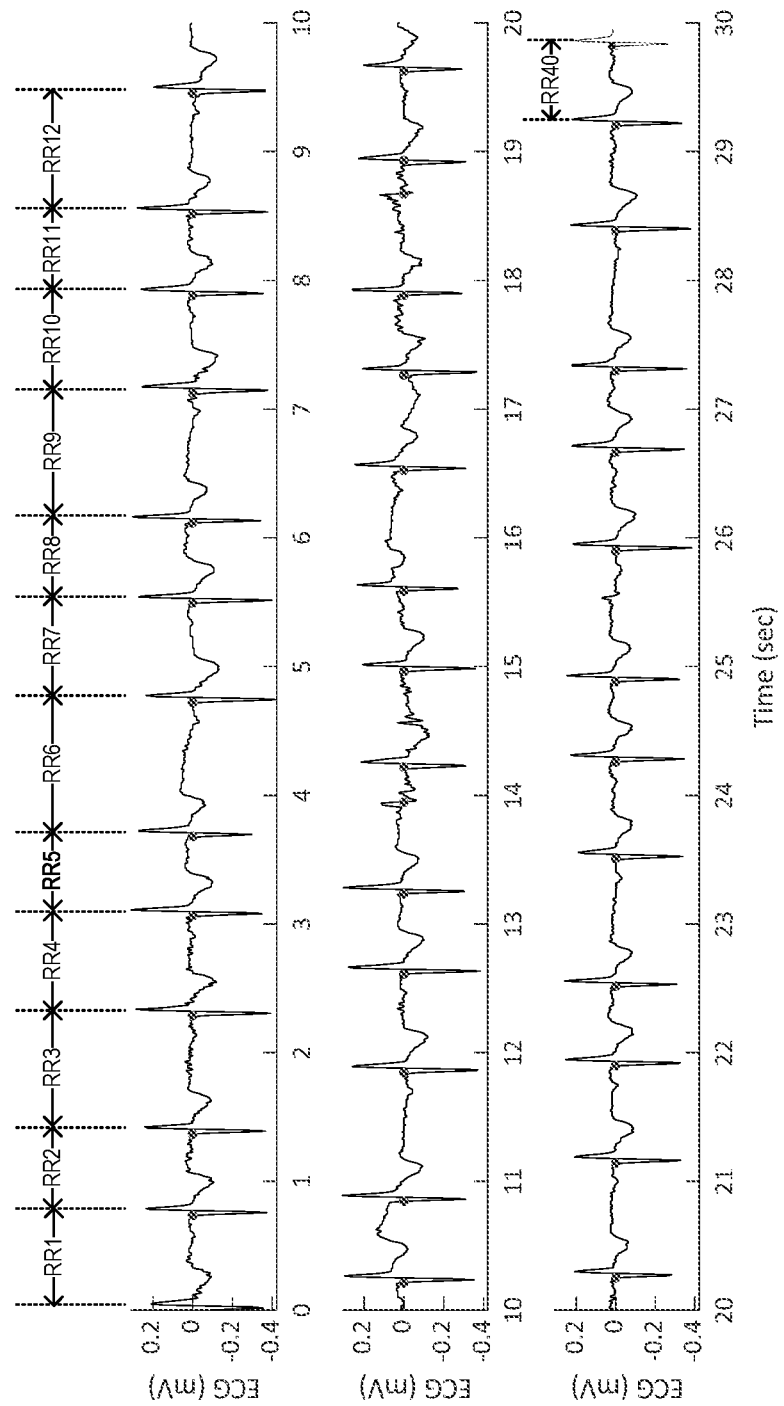
FIG. 1 includes an example an EGM segment within a thirty-second window leading up to a detection of a potential AF episode.

It is well known that each cardiac cycle represented within an electrogram (EGM) or an electrocardiogram (ECG) typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart, which can also be referred to as cardiac electrical signals, or the like.

The R-wave is the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration between a pair of consecutive R-waves. As noted above, in the Background, a common technique for detecting AF is based on measures of R-R interval variability. However, relying solely on R-R interval variability for detecting AF can lead to many false positive AF detections. This is because relying solely on R-R interval variability will not detect regularly irregular patterns of R-R intervals that are not indicative of AF, but rather, may result if multiple atrial foci of activity take turns activating the ventricles. As will be described in additional detail below, certain embodiments of the present technology described herein provide for improved AF discrimination by distinguishing between regularly irregular patterns of R-R intervals, which are not indicative of AF, and irregularly irregular patterns that are indeed indicative of AF. Beneficially, such embodiments can be used to reduce false positive AF detections and thereby increase the specificity of AF detections. More generally, embodiments of the present technology can be used to increase the specificity of arrhythmia detections.

In accordance with certain embodiments of the present technology, an ordered list of R-R intervals within a window leading up to a detection of a potential arrhythmia episode is obtained, wherein each of the R-R intervals has a respective duration. The potential arrhythmia episode, which can also be referred to as an arrhythmia trigger, may occur because R-R interval variability exceeded a specified threshold for at least a specified period of time, and/or using some other technique for detecting potential arrhythmia episodes. Such a window can be defined, for example, as a specified number N of R-R intervals leading up to the detection of the potential arrhythmia episode. Such a window can alternatively be defined, for example, as a specified number N of seconds leading up to the detection of the detection of the potential arrhythmia episode. For more specific examples, N can equal thirty (30), in which case the aforementioned window can include thirty R-R intervals leading up to the potential episode arrhythmia episode, or the R-R intervals within a thirty second window leading up to the detection of the potential arrhythmia episode. The use of smaller or larger values for N are also within the scope of the embodiments described herein.

In certain embodiments, a measure of a dominant repeated R-R interval pattern within the window is determined and compared to pattern threshold. If the measure of the dominant repeated R-R interval pattern is below the pattern threshold, then it is determined that the detection of the potential arrhythmia episode does not correspond to an actual arrhythmia episode. Conversely, if the measure of the dominant repeated R-R interval pattern is above the pattern threshold, then there is an increased level of confidence that the detected potential arrhythmia episode corresponded to an actual arrhythmia episode, i.e., there is an increased level of confidence that the detected potential arrhythmia episode corresponds to a true positive detection. While embodiments of the present technology can be used to increase the specificity of arrhythmia detections for various different types of arrhythmias, such embodiments are especially useful for increasing the specificity of AF detections. Accordingly, in the following discussion the type of arrhythmia discussed is often AF. However, it should be understood that embodiments of the present technology can also be used to increase the specificity of arrhythmia detections for various other types of arrhythmias besides AF, such as, but not limited to, bradycardia, asystole, atrial tachycardia (AT), ventricular tachycardia (VT), and ventricular fibrillation (VF). Further, it is noted that the terms "arrhythmia episode", "arrhythmic episode", "episode of an arrhythmia", and the like, are considered to be interchangeable.

FIG. 1 includes an example an EGM segment within a thirty (30) second window leading up to a detection of a potential AF episode, wherein there are forty (40) R-R intervals within the window. A detection of a potential AF episode may also be referred to herein as a potential AF detection, an AF trigger, or the like. In order to fit the EGM segment on a single page, the EGM segment in FIG. 1 is separated into three separate ten second panels that are shown one above the other. Example R-R intervals are labeled within FIG. 1. The R-R intervals within the top one of the three ten second panels are labeled RR1, RR2, RR3, ... RR12, wherein RR1 corresponds to the R-R interval number 1, the RR2 corresponds to the R-R interval number 2, the RR3 corresponds to the RR interval number 3, .... RR12 corresponds to the R-R interval number 12. Except for the RR40, which corresponds to the R-R interval number 40, the R-R intervals in the other two ten second panels are not labeled so as to minimize clutter in FIG. 1.

The table in FIG. 2 incudes a list of the forty R-R intervals within the thirty-second window shown in FIG. 1. What is shown in the rightmost column in FIG. 2 is an example of an ordered list of R-R intervals within a window leading up to a detection of a potential AF episode, wherein each of the R-R intervals has a respective duration. Referring to FIG. 2, the duration for the RR1 is 734.4 milliseconds (ms), the duration of the RR2 is 632.8 ms, the duration of the RR3 is 921.9 ms, ... the duration of the RR40 is 625.0. As can be appreciated from FIG. 2, the minimum R-R interval duration shown therein is 275.8 ms, and the maximum R-R interval duration shown therein is 1085.9 ms. It can be appreciated from FIG. 2 that there is very high R-R interval variability, which is what led to the detection of the potential AF episode.

Figure 3:
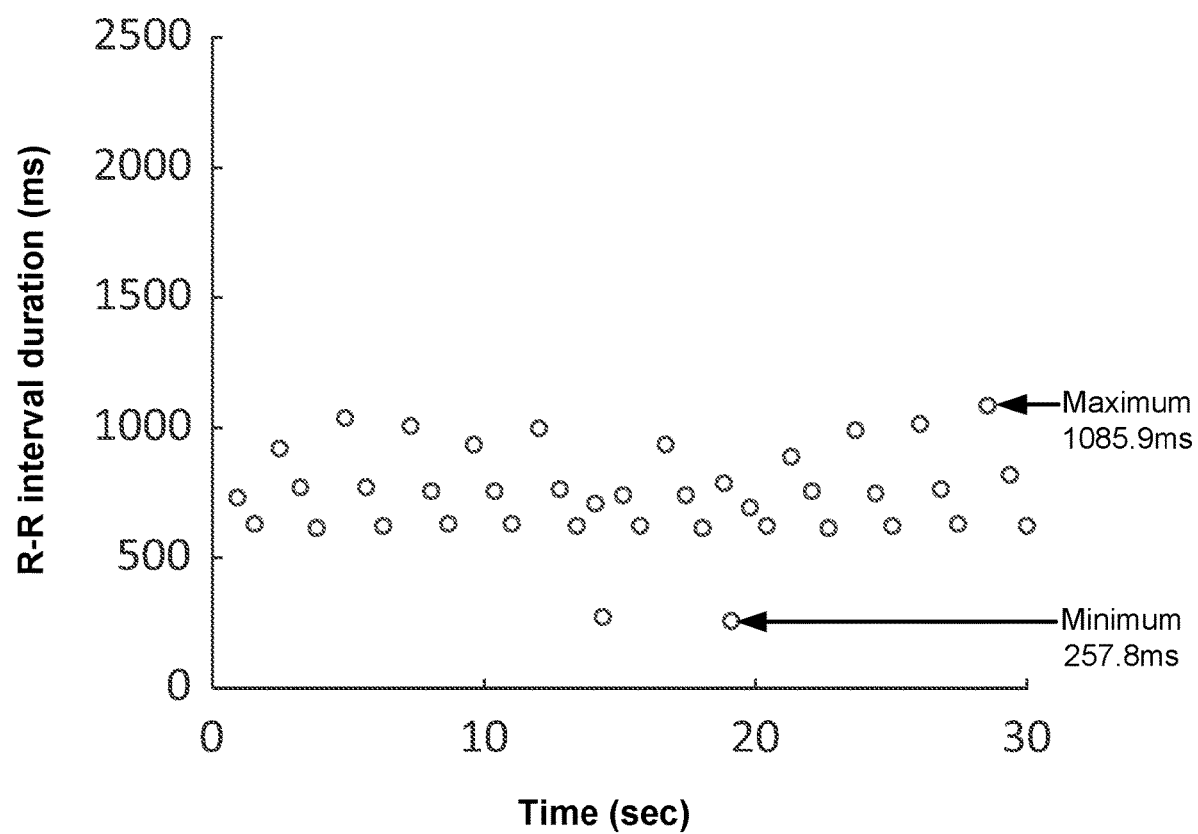
FIG. 3 is a graph showing the forty R-R intervals (within the thirty-second window shown in FIG. 1 and listed in the table in FIG. 2) versus time.

FIG. 3 is a graph showing the forty R-R intervals (within the thirty-second window shown in FIG. 1 and listed in the table in FIG. 2) versus time. The minimum R-R interval duration (275.8 ms) and the maximum R-R interval duration (1085.9 ms) are pointed to by arrows, as was also the case in FIG. 2. It can also be appreciated from FIG. 3 that there is very high R-R interval variability, which is what led to the detection of the potential AF episode.

Figure 4A:
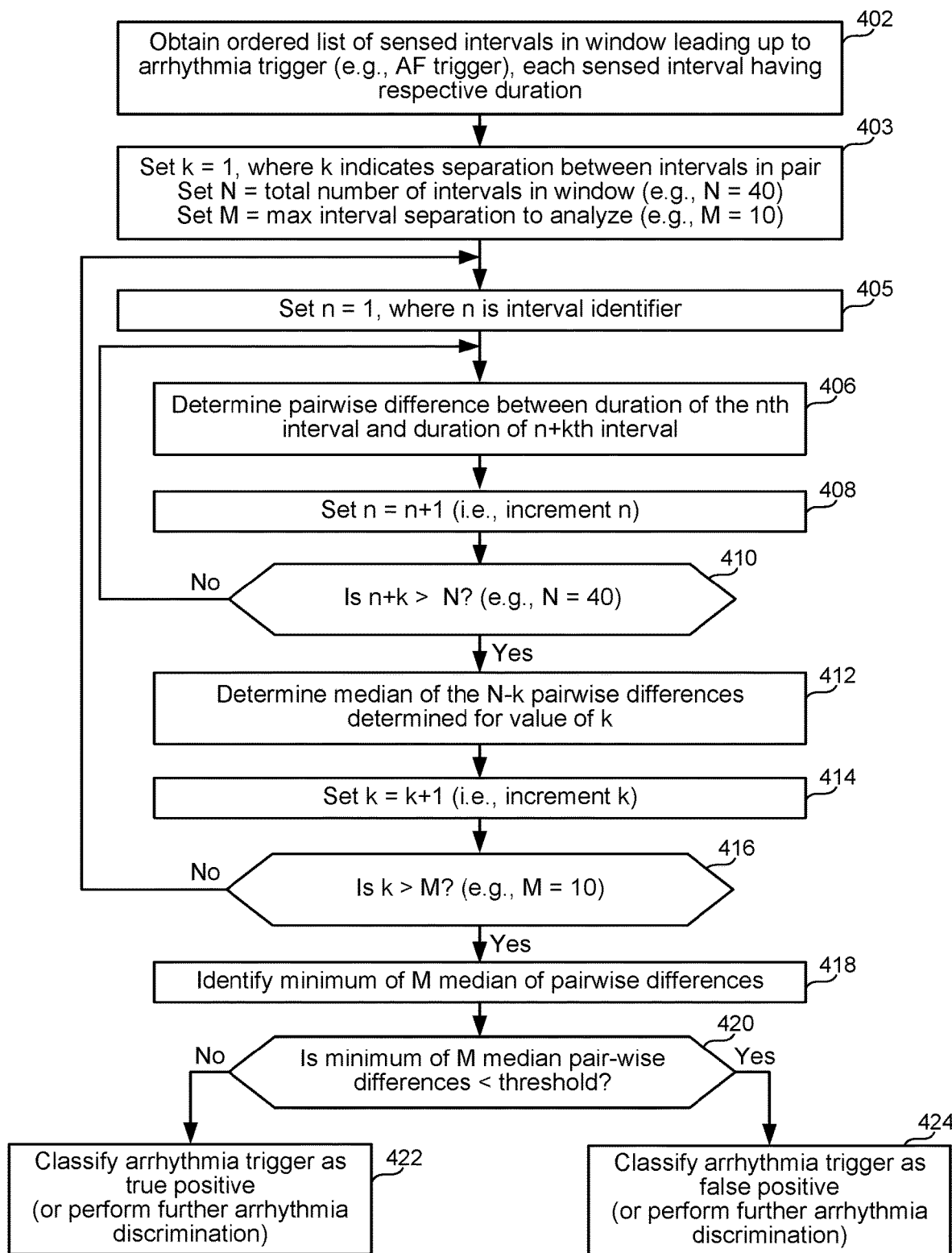
FIGS. 4A, 4B, and 4C are high level flow diagrams used to summarize various different methods of the present technology for improving arrhythmia episode detection specificity.

In accordance with certain embodiments of the present technology, an ordered list of R-R intervals within a window leading up to a detection of a potential AF episode (or other type of potential arrhythmia episode) is obtained and analyzed to determine whether there is regularly irregular pattern hidden therein, which is indicative of the detection of a potential AF episode being a false positive detection. More specifically, in certain embodiments, in order to determine whether a regularly irregular pattern of R-R intervals is present within the window, pairwise differences are determined between pairs of R-R intervals that are one interval apart, two intervals apart, three intervals apart, ... and M intervals apart. This results in M sets of pairwise differences. For example, assuming there are forty R-R intervals within the window being analyzed (as was the case in the example widow described above with reference to FIGS. 1 and 2), the $1^{st}$ set of pairwise differences can include the difference between the $1^{st}$ and $2^{nd}$ R-R intervals, the difference between the $2^{nd}$ and $3^{rd}$ R-R intervals, the difference between the $3^{rd}$ and $4^{th}$ RR-intervals, ... the difference between the $39^{th}$ and $40^{th}$ R-R intervals. The $2^{nd}$ set of pairwise differences can include the difference between the $1^{st}$ and $3^{rd}$ R-R intervals, the difference between the $2^{nd}$ and $4^{th}$ R-R intervals, the difference between the $3^{rd}$ and $5^{th}$ RR-intervals, ... the difference between the $38^{th}$ and $40^{th}$ R-R intervals. The $3^{rd}$ set of pairwise differences can include the difference between the $1^{st}$ and $4^{th}$ R-R intervals, the difference between the $2^{nd}$ and $5^{th}$ R-R intervals, the difference between the $3^{rd}$ and $6^{th}$ RR-intervals, ... the difference between the $37^{th}$ and $40^{th}$ R-R intervals. The $M^{th}$ set of pairwise differences can include the difference between the $1^{st}$ and $M^{th}$ R-R intervals, the difference between the $2^{nd}$ and $(M+1)^{th}$ R-R intervals, the difference between the $3^{rd}$ and $(M+2)^{th}$ RR-intervals, ... the difference between the $(40-M)^{th}$ and $40^{th}$ R-R intervals. For each set of pairwise intervals, of the M sets of pairwise intervals, a median (or an indicator of the median) of the set is determined, wherein a relatively low median (or indicator thereof) is indicative of there being a hidden pattern (most likely meaning that AF did not occur), and relative high median (or indicator thereof) is indicative of there being no regular irregular pattern (most likely meaning that AF actually did occur). In certain embodiments, the minimum median (or indicator thereof) for the M sets is identified and compared to a pattern threshold, wherein the minimum median (or indicator thereof) is an example of a measure of the dominant repeated pattern within the window. If the minimum median (or indicator thereof) is below the pattern threshold, then it is determined that the detection of the potential AF episode does not correspond to an actual AF episode. Conversely, if the minimum median (or indicator thereof) is above the pattern threshold, then there is an increased level of confidence that the detected potential AF episode corresponded to an actual AF episode, i.e., there in increased level of confidence that the detected potential AF episode corresponds to a true positive detection. Additional details of the embodiments summarized above are described below with reference to the high level flow diagram in FIG. 4A. More specifically, FIG. 4A is used to summarize certain methods of the present technology for improving AF episode detection specificity. Such a method may be triggered in response to a detection of a potential AF episode.

Referring to FIG. 4A, step 402 involves obtaining an ordered list of R-R intervals within a window leading up to a detection of potential arrhythmia episode (e.g., a potential AF episode), wherein each of the R-R intervals has a respective duration. The ordered list of R-R intervals can be obtained, for example, by identifying R-waves within an EGM or ECG segment, and determining intervals between consecutive ones of the R-waves to thereby produce the ordered list of R-R intervals. Such R-waves can be identified within the EGM or ECG segment by comparing the EGM or ECG segment, or samples thereof, to an R-wave sensing threshold, and identifying R-waves when the R-wave sensing threshold is reached or exceeded. Other variations are also possible and within the scope of the embodiments described herein. For example, R-waves can alternatively or additionally be identified using R-wave or QRS complex morphology templates.

An example of the ordered list of R-R interval within a window leading up to a detection of a potential AF episode is shown in FIG. 2, as noted above. The ordered list of R-R intervals, obtained at step 402, would preferably include only true R-R intervals. However, due to T-wave and/or P-wave oversensing, the ordered list of intervals obtained at step 402 may also include one or more over-sensed R-R intervals. In other words, the ordered list of R-R intervals, included in the window leading up to the detection of the potential arrhythmia episode, e.g., a potential AF episode (aka an "AF trigger"), in addition to including true R-R intervals, may also include one or more over-sensed R-R intervals that may be present, e.g., if one or more P-waves and/or T-waves are mistakenly identified as R-waves. In order to maximize the specificity of the methods summarized with reference to FIG. 4A, one or more techniques for identifying and removing over-sensed R-R intervals can be performed prior to step 402, as part of step 402, or between step 402 and the next step 403.

Still referring to FIG. 4A, at step 403 the values of various variables are specified. More specifically, at step 403 there is a setting of k=1, where k indicates the separation between R-R intervals in a pair of R-R intervals. Further, a value for N is specified, wherein N is the total number of R-R intervals within the window leading up to the detection of the potential AF episode. In the example discussed above with reference to FIGS. 1 and 2, N=40. Additionally, at step 403 M is set to the maximum interval separation that is to be analyzed. In accordance with certain embodiments, M is an integer that is at least equal to 4. In certain examples described herein, M is set to 10, i.e., M=10 in such examples.

Step 405 involves setting n=1, where n is an interval identifier.

Step 406 involves determining a pairwise difference between the duration of the nth interval and the duration of the n+$k^{th}$ interval. Presuming n=1 and k=1 the first time that step 406 is performed, then step 406 involves determining the pairwise difference between the duration of the $1^{st}$ interval and the duration of the $2^{nd}$ interval.

At step 408 the value for n is incremented by setting n=n+1. Thus, the first time step 408 is performed, n=1+1, thereby setting n=2.

At step 410 there is a determination of whether n+k is greater than to N. Presuming N=40, the first time that step 410 is performed n+k will equal 3, which is less than N (i.e., is less than 40), resulting in the answer to the determination at step 410 being No. If the answer to the determination at step 410 is No, the flow returns to step 406. This will result in N-k pairwise differences being determined before the answer to the determination at step 410 is eventual Yes, at which point flow goes to step 412. Accordingly, for n=1, the iterations of steps 406 through 410 will result in a pairwise difference between the $1^{st}$ and $2^{nd}$ R-R intervals, a pairwise difference between the $2^{nd}$ and $3^{rd}$ R-R intervals, a pairwise difference between $3^{rd}$ and $4^{th}$ R-R intervals, ... and a pairwise difference between the $39^{th}$ and $40^{th}$ R-R intervals, resulting in a total of 39 pairwise differences being determined for k=1. More generally, N-k pairwise differences are determined before the answer to the determination at step 410 is Yes, resulting in flow going to step 412.

At step 412 there is a determination of the median of the N-k pairwise differences determined for the value of k. In accordance with certain embodiments, this median value identified at step 412 is saved at least temporarily so that it can be compared to later determined median values, which are determined at later instances of step 412. To find the median of N-k pairwise differences for the value of k, the pairwise differences can be arranged in order from least to greatest, and the median is the value that is halfway into the set, i.e., the middlemost value. If there is an even number of values in the data set, then the median can be determined by determining the mean (average) of the two middlemost numbers, or selecting either one of the two middlemost numbers, depending upon the specific implementation.

At step 414 the value for k is incremented by setting k=k+1. Thus, the first time step 414 is performed, k=1+1, thereby setting k=2.

At step 416 there is a determination of whether k is greater than M. If the answer to the determination at step 416 is No, then flow returns to step 405, where n is reset to 1.

Steps 406 through 410 are then repeated for k=2, which will result determinations of a pairwise difference between the $1^{st}$ and $3^{rd}$ R-R intervals, a pairwise difference between the $2^{nd}$ and $4^{th}$ R-R intervals, a pairwise difference between $3^{rd}$ and $5^{th}$ R-R intervals, . . . and a pairwise difference between the $38^{th}$ and $40^{th}$ R-R intervals, resulting in a total of 38 pairwise differences. Then, at the next instance of step 412 there is a determination of the median of the 38 pairwise differences determine for the value of k=2.

At the next instance of step 414 the value for k is incremented by setting k=k+1. Thus, the second time step 414 is performed, k=2+1, thereby setting k=3.

At the next instance of step 416 there is a determination of whether k (which is now equal to 3) is greater than M. Presuming M=10, the answer to the determination at step 416 is No, returning flow to step 405, where n is reset to 1.

Steps 406 through 410 are then repeated for k=3, which will result determinations of a pairwise difference between the $1^{st}$ and $4^{th}$ R-R intervals, a pairwise difference between the $2^{nd}$ and $5^{th}$ R-R intervals, a pairwise difference between $3^{rd}$ and $6^{th}$ R-R intervals, . . . and a pairwise difference between the $37^{th}$ and $40^{th}$ R-R intervals, resulting in a total of 37 pairwise differences. Then, at the next instance of step 412 there is a determination of the median of the 37 pairwise differences determine for the value of k=3.

Assuming M=10, ten instances of step 412 will be performed before the answer to the determination at step 416 is Yes, thereby resulting in 10 median pairwise differences being determined (one for each of k=1, k=2, k=3 . . . , and k=10) before flow goes to step 418. At step 418 the minimum of the median of the pairwise differences is identified, wherein the value of k corresponding to the minimum of the median of the pairwise differences corresponds to the dominant repeated R-R interval pattern. For example, if the minimum of the 10 median of the pairwise differences corresponds to k=3, then it can be said that most dominant pattern within the window is an R-R interval pattern that repeats every three R-R intervals. This happens to be the case in the example shown above in FIGS. 1 and 2. Referring briefly back to FIG. 2, it can be appreciated that the duration of $1^{st}$ R-R interval is 734.4 ms, the duration of the $4^{th}$ R-R interval is 773.4, the duration of the $7^{th}$ R-R interval is 773.4 ms, the duration of the $10^{th}$ R-R interval is 757.8 ms, the duration of the $13^{th}$ R-R interval is 757.8 ms, . . . the duration of the $36^{th}$ R-R interval is 765.6 ms, the duration of the $39^{th}$ R-R interval is 820.3 ms.

Returning to the discussion of FIG. 4A, after the minimum of the M median pairwise differences is identified at step 418, flow then goes to step 420.

At step 420 there is a determination of whether the minimum of the M median pairwise differences (identified at step 418) is less than a corresponding threshold. If the answer to the determination at step 420 is No, that is indicative of a no hidden pattern being identified, and flow goes to step 422. At step 422 the potential arrhythmia episode (aka arrhythmia trigger) is classified as a true positive, or further arrhythmia discrimination is performed. If the answer to the determination at step 420 is Yes, that is indicative of a hidden regular irregular pattern being identified, and flow goes to step 424. At step 424 the potential arrhythmia episode (aka arrhythmia trigger) is classified as a false positive, or further arrhythmia discrimination is performed. In specific embodiments used for AF discrimination, at step 422 the potential AF episode (aka AF trigger) is classified as a true positive, or further AF discrimination is performed. If the answer to the determination at step 420 is Yes, that is indicative of a hidden regular irregular pattern being identified, and flow goes to step 424; and at step 424 the potential arrhythmia episode (aka arrhythmia trigger) is classified as a false positive, or further arrhythmia discrimination is performed.

The method summarized with reference to FIG. 4A essentially performs a pattern recognition, wherein the method first calculates the median R-R interval difference between every interval and the next interval (interval 1 vs. 2, 2 vs. 3, 3 vs. 4, etc. . . . ), i.e., between intervals that are 1 interval apart. This calculation is repeated for intervals that are 2 intervals apart (interval 1 vs. 3, 2 vs. 4, etc. . . . ), 3 intervals apart, . . . , and up to 10 intervals apart (or some other value for M, where M is an integer that is at least 4). This results in 10 (or more generally M) median pairwise differences across all intervals in the window preceding the AF trigger marker. The minimum of these pairwise differences across all intervals is then used to identify the interval period of the dominant pattern. For example, a pattern that repeats itself every 3 intervals would result in the smallest median difference calculated between every interval versus 3 intervals later. If the "minimum median pairwise difference" is below a specified threshold, then the interval variability that caused the arrhythmia trigger (e.g., AF trigger) can be interpreted as actually be associated with a repeating pattern (e.g., false positive AF), and the arrhythmia trigger (e.g., AF trigger) can be rejected.

An example algorithm that can be used to determine a median of N−1 pairwise difference values is shown below, where the median is represented as a median percent difference.

Median Percent Difference=MEDIAN(100*|RR(n)−RR(n+1)|/RR(n)), for intervals n=1:N, where RR(n) is a nth R-R interval within the window, RR(n+1) is a $(n+1)^{th}$ R-R interval within the window,

|RR(n)−RR(n+1)| is the absolute value of RR(n)−RR(n+1), and

N is a total number of R-R intervals within the window.

The above calculation compares intervals separated by 1 interval, i.e., that are 1 interval apart. This calculation is then repeated for interval separations of 2 through 10, or more generally for 2 though M intervals apart. Expanding the calculation for all interval separations k=1:10, or more generally k=1:M the following equation is used:

Median Percent Difference for k=MEDIAN(100*|RR(n)−RR(n+k)|/RR(n)), for intervals n=1:N and interval separations k=1:M.

This results in 10 median percent differences, each comparing intervals separated by 1 to 10 intervals. The minimum of these pairwise differences across all intervals is then used to identify the interval period of the dominant pattern (i.e., how many intervals it takes to repeat the pattern).

As noted above, the table in FIG. 2 incudes a list of the forty R-R intervals within a thirty-second window (shown in FIG. 1) leading up to a detection of a potential AF episode. Based on these forty R-R intervals, the mean percentage difference for intervals separated by 1 to 10 intervals, calculated using the above note equation, for interval pairs separated by 1, 2, . . . , 10 intervals are as follows: Median Percent Difference=[24.4%, 30.5%, 3.0%, 18.8%, 31.3%, 9.6%, 16.5%, 29.1%, 17.3%, 13.8%]. In this example, the minimum percent difference (3.0%) occurred when each interval was compared to the interval 3 intervals later (i.e., the 3$^{rd}$ of 10 median percent differences). Presuming the threshold is 6%, it can be appreciated that in this example the minimum median percent difference (i.e., 3.0%) is less than the threshold of 6%, and thus it can be concluded that the interval variability that caused the AF trigger was actually associated with a repeating pattern (i.e., false positive AF), and can be rejected.

To reduce processing time, the algorithm may stop calculating the median percent differences as soon as any median R-R interval difference or indicator thereof (e.g., median percent difference) below the threshold is observed. In other words, and more generally, instead of determining all M indicators, then identifying a minimum, and then comparing the minimum to a threshold, the following can be performed instead. Each time a new median R-R interval difference or indicator thereof (e.g., median percent difference) is determined for a value of k, that median R-R interval difference can be compared to the threshold, and then as soon as there is a determination that the median is below the threshold there can be a conclusion that the detection of the potential arrhythmia episode was a false positive arrhythmia detection (e.g., a potential AF episode was a false positive AF detection). If the determined median is not less than the threshold, then another value for k is picked and analyzed, until either there is the conclusion of a false positive arrhythmia detection or there are no more new values for k to pick and analyze. Using the example window described above with reference to FIGS. 1 and 2, only three median percent differences would need to be calculated (i.e., for values of k=1, 2, and 3) to reject an AF detection as a false positive. An example of such an alternative embodiment is described with reference to FIG. 4B.

Figure 4B:
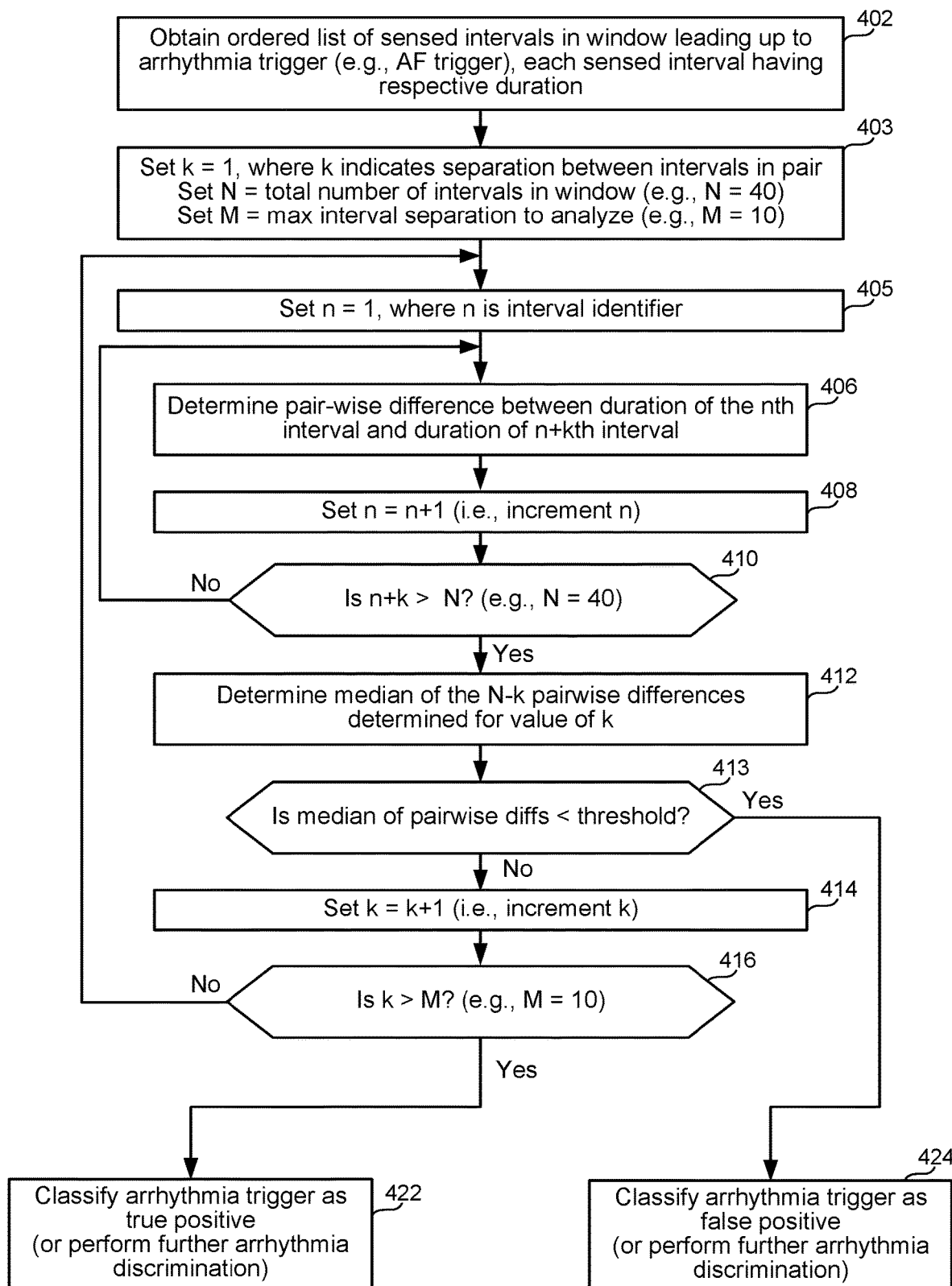

More specifically, FIG. 4B is used to summarize further methods of the present technology for improving arrhythmia episode detection specificity, wherein such a method may be triggered in response to a detection of a potential arrhythmia episode (e.g., a potential AF episode). The steps in FIG. 4B that are the same as those discussed above with reference to FIG. 4A are labeled the same, and need not be described in detail, since reference can be made to FIG. 4A for further details of such steps. Referring to FIG. 4B, steps 402, 403, 405, 406, 408, 410, and 412 are the same as those commonly numbered steps in FIG. 4A. The first time step 412 is performed, i.e., for k=1, there is a determination of the median of the N−k (i.e., N−1, e.g., if N=40 then N−k=39 when k=1) pairwise differences determine for the value of k=1, and the median of the N−1 pairwise differences (or an indicator thereof, such as the median percent difference) is compared to a threshold (e.g., 6%) at step 413. If the median is less than the threshold (i.e., if the answer to the determination at step 413 is Yes), then flow goes to step 424. At step 424 the potential arrhythmia episode (aka arrhythmia trigger) is classified as a false positive, or further arrhythmia discrimination is performed. If the median is not less than the threshold (i.e., if the answer to the determination at step 413 is No), then flow goes to step 414.

At step 414 the value fork is incremented by setting k=k+1. Thus, the first time step 414 is performed, k=1+1, thereby setting k=2.

At step 416 there is a determination of whether k is greater than M. If the answer to the determination at step 416 is No, then flow returns to step 405, where n is reset to 1.

Steps 406 through 410 are then repeated for k=2, which will result determinations of a pairwise difference between the 1$^{st}$ and 3$^{rd}$ R-R intervals, a pairwise difference between the 2$^{nd}$ and 4$^{th}$ R-R intervals, a pairwise difference between 3$^{rd}$ and 5$^{th}$ R-R intervals, . . . and a pairwise difference between the 38$^{th}$ and 40$^{th}$ R-R intervals, resulting in a total of 38 pairwise differences. Then, at the next instance of step 412 there is a determination of the median of the 38 pairwise differences determine for the value of k=2. Then, at the next instance of step 413, the median of the N−2 pairwise differences for k=2 (or an indicator thereof, such as the median percent difference) is compared to the threshold (e.g., 6%). If the median is less than the threshold (i.e., if the answer to the determination at step 413 is Yes), then flow goes to step 424, otherwise flow goes to step 414.

Presuming the method summarized with reference to FIG. 4B was performed using the R-R intervals within the example window (leading up to the detection of the potential AF episode) described above with reference to FIGS. 1 and 2, at the third instance of 413 (i.e., when k=3), the median percent difference for k=3 would be calculated to be 3.0%, resulting in the answer to the determination at step 413 being Yes, and the detection of the potential AF episode being classified as a false positive at step 424. Thus, it can be appreciated that for this example, the median percent differences would only need to be performed three values fork (i.e., for k=1, 2, and 3) before the method came to the false positive conclusion.

Figure 4C:
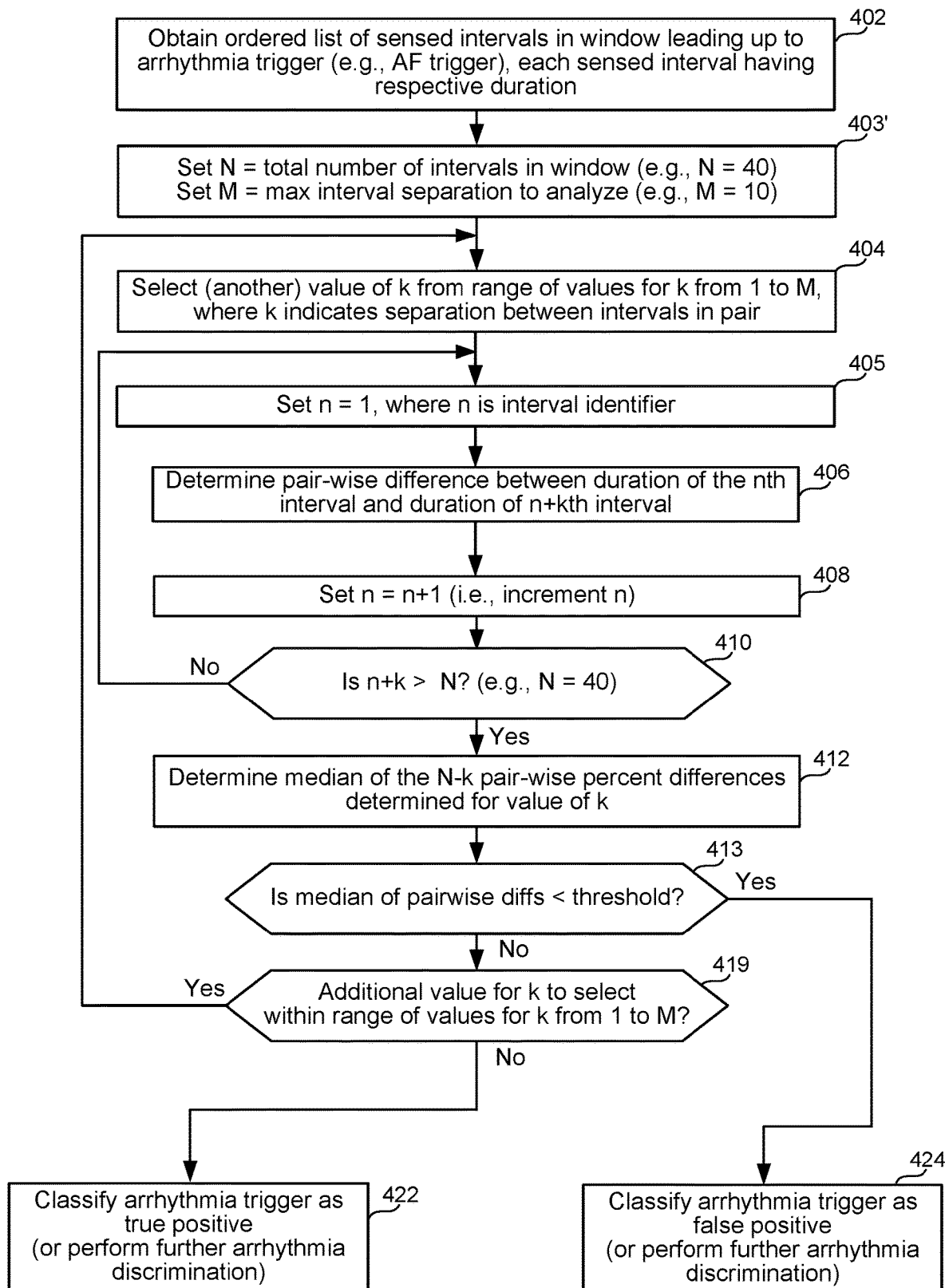

In the methods summarized with reference to with reference to FIG. 4B, a median of the pairwise differences for k=1 (or an indicator thereof) is first determined and compared to a threshold. If the median for k=1 is not less than the threshold, then a median of the pairwise differences for k=2 (or an indicator thereof) is then determined and compared to the threshold. If the median for k=2 is not less than the threshold, then a median of the pairwise differences for k=3 (or an indicator thereof) is then determined and compared to the threshold. This is repeated until a median (or an indicator thereof) is then than the threshold, or until there are not more values for k to analyze within the range of values for k (e.g., until k=M). Accordingly, in FIG. 4A, the initial value for k, that is selected from the range of values for k, is 1, and a median of the pairwise differences (or an indicator thereof) is determined for k=1. Then, if the median is not less than the threshold, 405-412 are repeated for another selected value of k, wherein the other selected value of k is produced by incrementing k so that k=k+1. In other words, different values for k are tested in ascending numerical order (starting with k=1), where k specifies how many intervals apart the R-R intervals are within each pairwise difference. In alternative embodiments, different values for k can be tested in descending numerical order, starting with k=M, where M is the maximum interval separation that is to be tested, e.g., M=10, or more generally, M is an integer that is at least 4. More generally, values for k can be tested in any order, including in ascending order, descending order, a random order, or some predetermined order. An example of a predetermined order for testing values for k within the range of 1 to 10 can be 6, 5, 7, 4, 8, 3, 9, 2, 1, 10. The flow diagram shown in FIG. 4C summarizes how this can achieved by selecting an initial (or another) value for k at each instance of step 404 (where k need not start with k=1, but may), and by determining at each instance of step 419 whether there is at least one additional value for k to select within the range of values for k from 1 to M. The method summarized with reference to FIG. 4B is actually a special case of the method summarized with reference to FIG. 4C, where the different values for k are tested in ascending order starting with k=1. Step 403' in FIG. 4C differs from step 403 in FIG. 4B by not initially setting k=1. Rather, any initial value for k (within the range of values from 1 to M) is selected at the first instance of step 404. The other steps in FIG. 4C that are numbered the same as they are in FIGS. 4A and 4B are the same as those steps described above with reference to FIGS. 4A and 4B and need not be described again.

In certain embodiments, pairwise differences between pairs of intervals that are k intervals apart are represented as percentages, and the medians of N−k pairwise difference percentages are represented as a percentage, i.e., a median percent difference for k, as was described above. In other embodiments, pairwise differences between pairs of intervals that are k intervals apart are represented as simple differences (i.e., |RR(n)−RR(n+k)|), aka deltas, that are not percentages, and the medians of N−k pairwise difference percentages are also represented as simple differences that are not percentages. In still other embodiments, pairwise differences between pairs of intervals that are k intervals apart are represented as ratios, as are the medians thereof. For example, rather than determining the difference between the nth and $(n+k)^{th}$ R-R interval by calculating RR(n)−RR(n+k), the difference can be represented by the ratio of RR(n)/RR(n+k) or RR(n+k)/RR(n), or by the higher of the two R-R intervals over the lower of the two R-R intervals being compared, or vice versa. The closer such a ratio is to unity (i.e., to the value one) the more likely a regular irregular pattern exists, which is an indicator of a non-AF event. Where ratios are used, the threshold used can be a threshold range, e.g., between 0.8 and 1.2, but not limited thereto. Other variations are also possible and within the scope of the embodiments described herein.

In accordance with certain embodiments, an IMD may perform one of the methods described above with reference to FIGS. 4A-4C in response to a potential arrhythmia episode (e.g., a potential AF episode) being detected. The detection of a potential arrhythmia episode can also be referred to as an arrhythmia trigger (e.g., AF trigger), as noted above. Such an IMD may be configured to transmit, to an external device that is communicatively coupled to a patient care network, data corresponding to a potential arrhythmia episode that is detected by the IMD. In certain such embodiments, the IMD does not (is prevented from) transmitting (to the external device that is communicatively coupled to the patient care network) data corresponding to a potential arrhythmia episode that is detected by the IMD, but is thereafter determined by the IMD as being a false positive detection.

The present technology described above was tested to determine whether and to what extend the present technology can be used to reduce the reporting of false positive AF detections. Such tests showed that embodiments of the present technology can be used to identify and thereby reject over thirty percent of false positive AF detections, compared to if AF detections were based solely on comparing measures of R-R interval variability to a variability threshold. Beneficially, the tests also showed the embodiments of the present technology incorrectly flagged less than one percent of AF detections as false positives, where they were actually true positives. Accordingly, embodiments of the present technology can be used to significantly increase AF detection specificity without significantly decreasing AF detection sensitivity.

Embodiments of the present technology can be used together with other types of technology that can be used to identify false positive arrhythmia detections, or more generally, can be used with other techniques used for improving arrhythmia detection and/or discrimination. For example, R-wave oversensing and/or R-wave understanding can be detected and accounted for and/or corrected for within an ordered list of sensed intervals, prior to or as part of an instance of step 402 in one or more of FIGS. 4A, 4B, and 4C. For another example, the ordered list of sensed intervals leading up to an arrhythmia trigger (e.g., AF trigger), that is obtained at step 402, could have been obtained after potential R-wave detections, and/or potential R-R intervals, were already subjected to other types of arrhythmia discriminators (e.g., AF discriminators), such as a sudden onset AF discriminator that scans beats within a window leading up to an AF detection to characterize the change of heart rate, and rejects an AF detection as a false positive if there is no significant change in heart rate leading up to the AF detection. Additionally, or alternatively, there can be a determination of whether R-wave under-sensing or intermittent AV conduction block beyond a corresponding threshold occurred within a window leading up to the arrhythmia detection (e.g., AF detection), and if at least one of those did occur, then the arrhythmia detection (e.g., AF detection) can be rejected as a false positive. Additionally, or alternatively, irregular R-R intervals due to T-wave and/or P-wave oversensing can be analyzed in a window leading up to the AF detection, and if the extent thereof exceeds a corresponding threshold, then the arrhythmia detection (e.g., AF detection) can be rejected as a false positive. These are just a few examples of the other types of arrhythmia discrimination techniques, which are time-based, that may be used prior to, leading up to, or after the use of the embodiments of the present technology described herein with reference to FIGS. 1-4C. Additionally, or alternatively, one or more morphology based arrhythmia discriminators (e.g., AF discriminators) may be used prior to or after use of the embodiments of the present technology described herein with reference to FIGS. 1-4C. For example, there can be a determination (based on EGM morphology) of whether P-wave oversensing beyond a corresponding threshold occurred within a window leading up to an AF detection, and if so, then the AF detection can be rejected as a false positive. Additionally, or alternatively, there can be a determination of whether actual P-waves beyond a specified threshold are present within the window leading up to an AF detection (because P-waves should not be present during an episode of AF), and if so, then the AF detection can be rejected as a false positive. The aforementioned AF discriminators can be applied in various different orders, together with at least one of the embodiments of the present technology described herein with reference to FIGS. 1-4C being used as just one of a plurality of AF discriminators. Other variations are also possible and within the scope of the embodiments of the present technology described herein.

The specific thresholds used to test the performance of embodiments of the present technology (e.g. 6%) and mentioned above can be more systematically optimized for a broader patient population, or for individual patients. Further, the maximum number M of interval separations analyzed, to determine if a regular irregular patterns is present, can also be similarly optimized. Accordingly, embodiments of the present technology described herein should not be limited to use with the exemplary thresholds of other values described herein.

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD). Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive arrhythmia detections (e.g., false positive AF detections) are highly undesirable, as the burden of sorting through large numbers of clinically irrelevant episodes of AF and/or other types of arrhythmias can be time consuming and costly. Where embodiments of the present technology are used by an ICD, or by an IMD in communication with an ICD, such embodiments can reduce how often defibrillation shocks are delivered in response to false positive AF detections. This is beneficial because defibrillation shocks are typically painful, and delivering such shocks in response to false positive AF detections subjects the patient to unnecessary shocks and may prematurely deplete the energy stored in a battery. It would also be possible for one or more of the methods described above with reference to FIGS. 4A-4C to be performed by an external device (e.g., a home monitor or external programmer) that obtains an EGM segment that precedes a potential AF detection from an IMD, or that receives an ordered list of R-R intervals (within a window leading up to a potential AF episode) from an IMD. It would also be possible that some of the steps in FIGS. 4A-4C be performed by an IMD and other steps be performed by an external device. Other variations are also possible and within the scope of the embodiments described herein.

Figure 5:
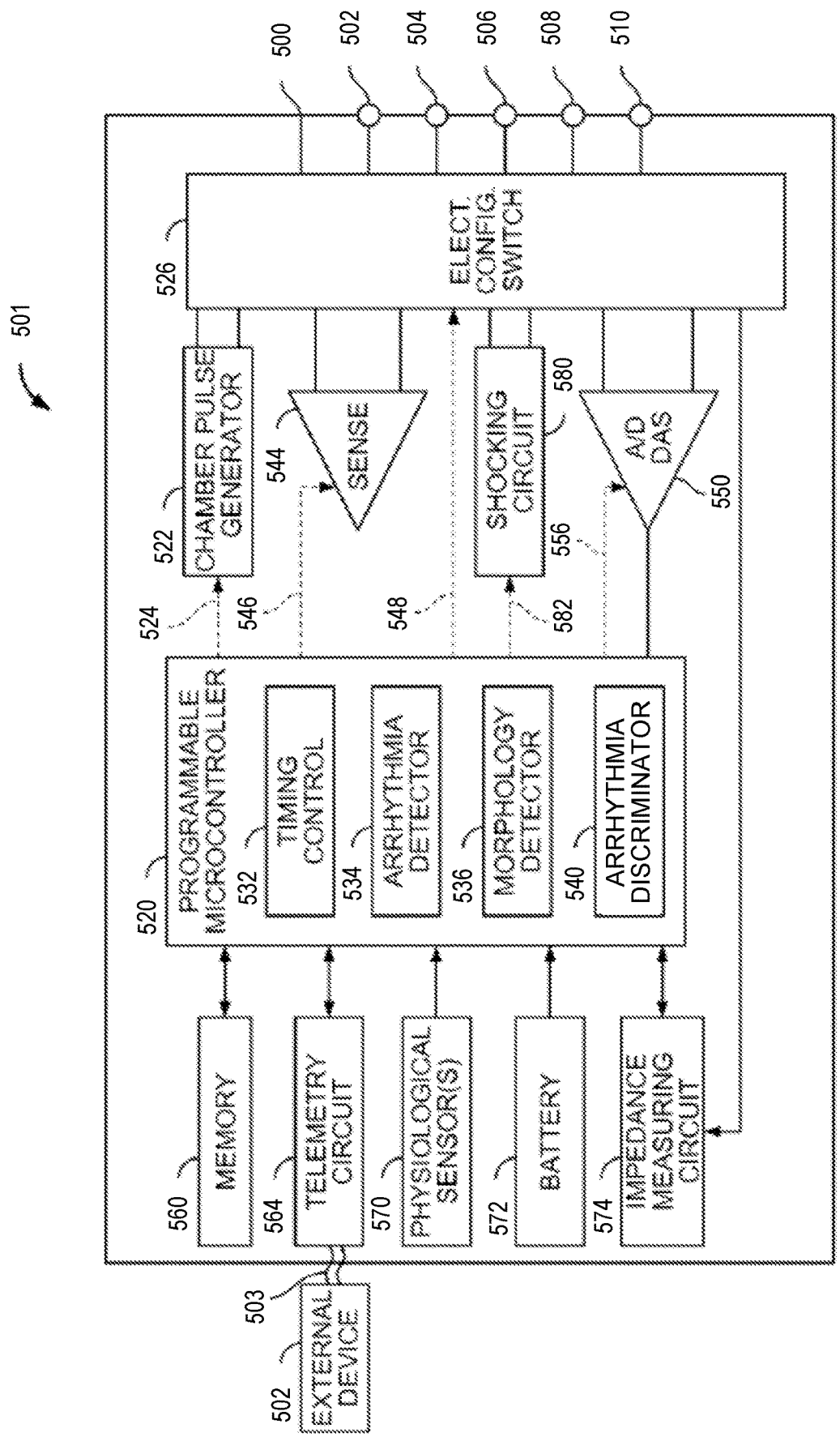
FIG. 5 shows a block diagram of one embodiment of an IMD that is implanted into a patient and can be used to implement certain embodiments of the present technology.

FIG. 5 shows a block diagram of one embodiment of an IMD that is implanted into a patient in accordance with a certain embodiment of the present technology. The IMD 501 may be implemented as a full-function biventricular pacemaker, equipped with both atrial and ventricular sensing and pacing circuitry for four chamber sensing and stimulation therapy (including both pacing and shock treatment). Optionally, the IMD 501 may provide full-function cardiac resynchronization therapy. Alternatively, the IMD 501 may be implemented with a reduced set of functions and components. For instance, the IMD may be implemented without pacing, e.g., if the IMD is an ICM. The IMD 501 can be coupled to one or more leads for single chamber or multi-chamber pacing and/or sensing. Alternatively, the IMD 501 can be an LCP that includes electrodes located on or very close to a housing 500 of the IMD 501.

The IMD 501 has a housing 500 to hold the electronic/computing components. The housing 500 (which is often referred to as the "can", "case", "encasing", or "case electrode") may be programmably selected to act as the return electrode for certain stimulus modes. The housing 500 may further include a connector (not shown) with a plurality of terminals 502, 504, 506, 508, and 510. The terminals may be connected to electrodes that are located in various locations on the housing 500 or to electrodes located on leads. The IMD 501 includes a programmable microcontroller 520 that controls various operations of the IMD 501, including cardiac monitoring and/or stimulation therapy. The microcontroller 520 includes a microprocessor (or equivalent control circuitry), RAM and/or ROM memory, logic and timing circuitry, state machine circuitry, and I/O circuitry.

The IMD 501 further includes a pulse generator 522 that generates stimulation pulses and communication pulses for delivery by one or more electrodes coupled thereto. The pulse generator 522 is controlled by the microcontroller 520 via a control signal 524. The pulse generator 522 may be coupled to the select electrode(s) via an electrode configuration switch 526, which includes multiple switches for connecting the desired electrodes to the appropriate I/O circuits, thereby facilitating electrode programmability. The switch 526 is controlled by a control signal 548 from microcontroller 520.

In the embodiment of FIG. 5, a single pulse generator 522 is illustrated. Optionally, the IMD may include multiple pulse generators, similar to the pulse generator 522, where each pulse generator is coupled to one or more electrodes and controlled by the microcontroller 520 to deliver select stimulus pulse(s) to the corresponding one or more electrodes.

The microcontroller 520 is illustrated as including timing control circuitry 532 to control the timing of the stimulation pulses (e.g., pacing rate, atrio-ventricular (AV) delay, atrial interconduction (A-A) delay, or ventricular interconduction (V-V) delay, etc.). The timing control circuitry 532 may also be used for the timing of refractory periods, blanking intervals, noise detection windows, evoked response windows, alert intervals, marker channel timing, and so on. The microcontroller 520 also has an arrhythmia detector 534 for detecting arrhythmia conditions and a morphology detector 536. The arrhythmia detector 534 can, for example, detect potential episodes of AF and/or other types of arrhythmias. Although not shown, the microcontroller 520 may further include other dedicated circuitry and/or firmware/software components that assist in monitoring various conditions of the patient's heart and managing pacing therapies. The microcontroller 520 is also shown as including an arrhythmia discriminator 540, which can be used to perform the embodiments of the present technology described above with reference to FIGS. 1-4C, e.g., to determine whether one or more potential episodes of AF and/or other types of arrhythmias are false positives. The arrhythmia discriminator 540 can more generally be implemented using hardware, software, firmware, and/or combinations thereof. The microcontroller can include a processor. The microcontroller, and/or the processor thereof, can be used to perform the methods of the present technology described herein.

The IMD 501 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 520, or as software/firmware instructions programmed into and executed by the microcontroller 520. Alternatively, the modem may reside separately from the microcontroller as a standalone component.

The IMD 501 includes a sensing circuit 544 selectively coupled to one or more electrodes, that perform sensing operations, through the switch 526 to detect the presence of cardiac activity in the right chambers of the heart. The sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 526 determines the sensing polarity of the cardiac signal by selectively closing the appropriate switches. In this way, the clinician may program the sensing polarity independent of the stimulation polarity.

The output of the sensing circuit 544 is connected to the microcontroller 520 which, in turn, triggers or inhibits the pulse generator 522 in response to the presence or absence of cardiac activity. The sensing circuit 544 receives a control signal 546 from the microcontroller 520 for purposes of controlling the gain, threshold, polarization charge removal circuitry (not shown), and the timing of any blocking circuitry (not shown) coupled to the inputs of the sensing circuitry.

In the embodiment of FIG. 5, a single sensing circuit 544 is illustrated. Optionally, the IMD may include multiple sensing circuits, similar to the sensing circuit 544, where each sensing circuit is coupled to one or more electrodes and controlled by the microcontroller 520 to sense electrical activity detected at the corresponding one or more electrodes. The sensing circuit 544 may operate in a unipolar sensing configuration or in a bipolar sensing configuration.

The IMD 501 further includes an analog-to-digital (ND) data acquisition system (DAS) 550 coupled to one or more electrodes via the switch 526 to sample cardiac signals across any pair of desired electrodes. Data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). Data acquisition system 550 is controlled by a control signal 556 from the microcontroller 520.

The microcontroller 520 is coupled to a memory 560 by a suitable data/address bus. The programmable operating parameters used by the microcontroller 520 are stored in memory 560 and used to customize the operation of the IMD 501 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 501 may be non-invasively programmed into memory 560 through a telemetry circuit 564 in telemetric communication via a communication link 503 with an external device 554. The telemetry circuit 564 allows intracardiac electrograms and status information relating to the operation of the IMD 501 (as contained in the microcontroller 520 or memory 560) to be sent to the external device 554 through the communication link 503. The telemetry circuit 564 can also be referred to as a transceiver 564.

The IMD 501 can save within the memory 560, and/or transmit to an external device (e.g., 502), data corresponding one or more arrhythmia episodes detected by the IMD 501, so that the data is available at a later time for further analysis. If the IMD 501 determines that a detection of the arrhythmia episode does not correspond to an actual arrhythmia episode, the IMD can allow data corresponding to the potential arrhythmia episode to be overwritten in the memory 560 and/or can prevent data corresponding to the potential arrhythmia episode from being transmitted to an external device using the transceiver 564.

The IMD 501 can further include magnet detection circuitry (not shown), coupled to the microcontroller 520, to detect when a magnet is placed over the unit. A magnet may be used by a clinician to perform various test functions of IMD 501 and/or to signal the microcontroller 520 that the external device 554 is in place to receive or transmit data to the microcontroller 520 through the telemetry circuit 564.

The IMD 501 can further include one or more physiological sensors 570. Such sensors are commonly referred to as "rate-responsive" sensors because they are typically used to adjust pacing stimulation rates according to the exercise state of the patient. However, the physiological sensor(s) 570 may further be used to detect changes in cardiac output, changes in the physiological condition of the heart, or diurnal changes in activity (e.g., detecting sleep and wake states). Signals generated by the physiological sensor(s) 570 are passed to the microcontroller 520 for analysis. The microcontroller 520 responds by adjusting the various pacing parameters (such as rate, AV Delay, V-V Delay, etc.) at which the atrial and ventricular pacing pulses are administered. While shown as being included within the IMD 501, one or more physiological sensor(s) 570 may be external to the IMD 501, yet still be implanted within or carried by the patient. Examples of physiologic sensors include sensors that, for example, sense respiration rate, pH of blood, ventricular gradient, activity, position/posture, minute ventilation (MV), and so forth.

A battery 572 provides operating power to all of the components in the IMD 501. The battery 572 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 572 also desirably has a predictable discharge characteristic so that elective replacement time can be detected. As one example, the IMD 501 employs lithium/silver vanadium oxide batteries.

The IMD 501 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used. In this embodiment the IMD 501 further includes a shocking circuit 580 coupled to the microcontroller 520 by a data/address bus 582.

The embodiments of the present technology described above were primarily described as being used with an implantable medical device or system that monitors HR and/or for one or more types of arrhythmic episodes based on sensed intervals (e.g., R-R intervals). Such embodiments of the present technology can alternatively be used with a non-implantable device or system (aka an external device or system) that includes at least two electrodes in contact with a person's skin and is used to monitor HR and/or for one or more types of arrhythmic episodes based on sensed intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuitry (which can also be referred to as a sensing circuit) coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for AF and/or other types of arrhythmia(s) and determine when there is a false positive detection. A user wearable device can both obtain a signal indicative of electrical activity of a patient's heart and monitor a person's HR and/or for arrhythmia(s) based on R-R intervals obtained from the obtained signal. Alternatively, a user wearable device can be communicatively coupled to another external device, such as a smartphone or tablet computer, and the other external device can obtain the signal from the user wearable device and monitor a person's HR and/or for arrhythmia(s) based on R-R intervals and/or the like. The user wearable device or other external device or system can determine when there may be a false positive arrhythmia detection. Other implementations of such an external device or system are also possible and within the scope of the embodiments described herein.

Figure 6:
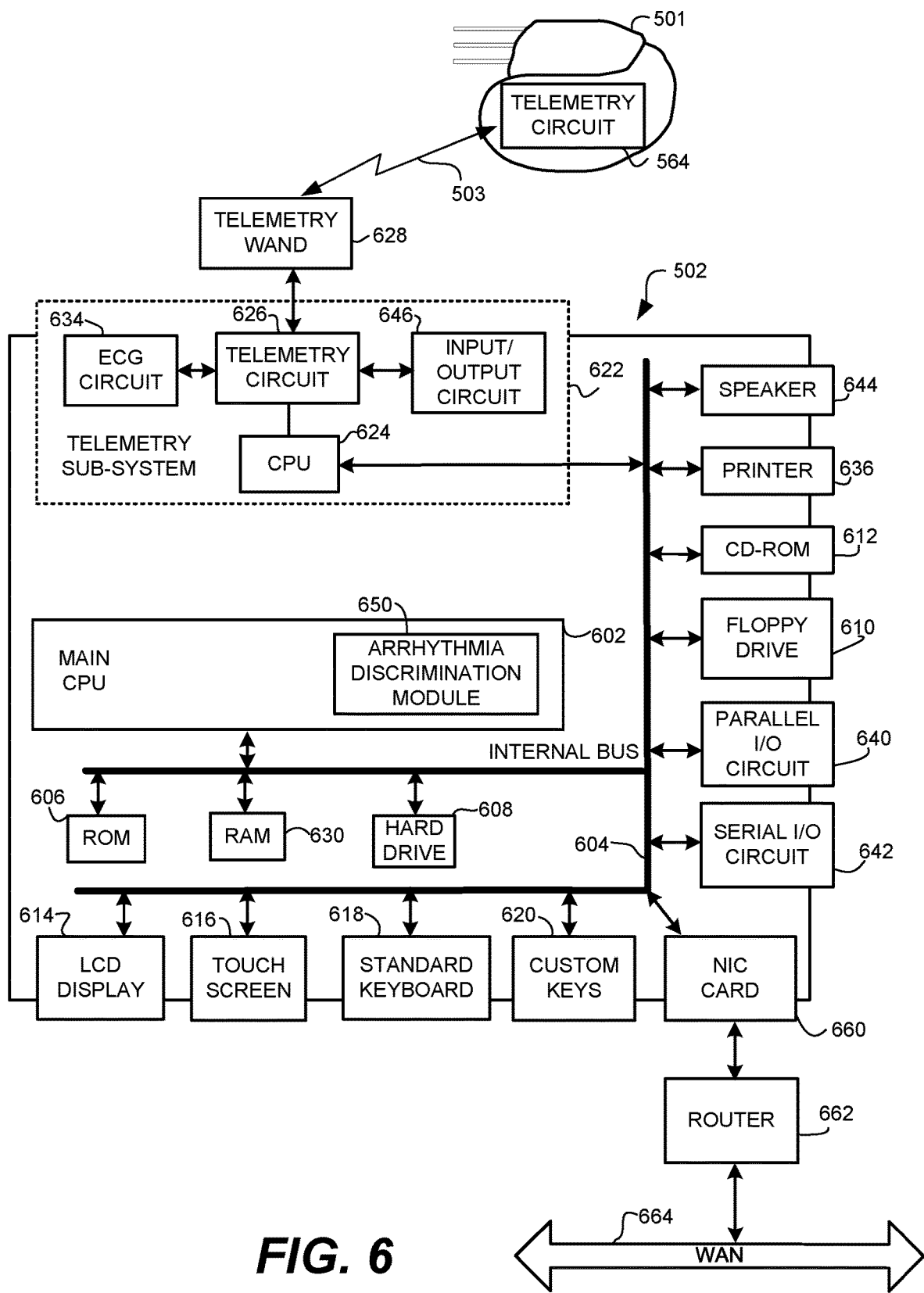
FIG. 6 shows a block diagram of one embodiment of an external device for use in communicating with and/or programming the IMD introduced in FIG. 5, and which can be used to implement certain embodiments of the present technology.

FIG. 6 illustrates example components of an example external device 554 for use in communicating with and/or programming the IMD 501. In certain embodiment, the external device 502 can be used to analyze EGM segments obtained and stored by the IMD 501. More generally, the external device 502 may permit a physician or other authorized user to program the operation of the IMD 501 and to retrieve and display information received from the IMD 501 such as EGM data and device diagnostic data. Additionally, the external device 502 may include an ECG circuit 634 to receive and display ECG data from separate external ECG leads that may be attached to the patient. Further, the external device 502 is capable of causing the IMD to perform functions necessary to complete certain algorithms of the present invention. Depending upon the specific programming of the programmer, external device 502 may also be capable of processing and analyzing data received from the IMD 501 and from ECG leads (not shown) to, for example, render preliminary diagnosis as to medical conditions of the patient or to the operations of the IMD 501. Such leads can also be used to obtain an actual surface ECG, from which an ordered list of R-R intervals leading up to a potential arrhythmia detection may be obtained. Additionally, the external device 502 is capable of accepting the various user inputs that are accepted in accordance with embodiments of the present invention described above.

Now, considering the components of the external device 502 by reference to FIG. 6, operations of the external device 502 can be controlled by a CPU 602, which may be a generally programmable microprocessor or microcontroller or may be a dedicated processing device such as an Application Specific Integrated Circuit (ASIC) or the like. Software instructions to be performed by the CPU can be accessed via an internal bus 604 from a Read Only Memory (ROM) 606 and Random Access Memory (RAM) 630. Additional software may be accessed from a hard drive 608, floppy drive 610, and CD ROM drive 612, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 614 or another suitable computer display device. To this end, the CPU may, for example, display a menu of specific programming parameters of the IMD 501 to be programmed or may display a menu of types of diagnostic data to be retrieved and displayed. In response thereto, the physician enters various commands via either a touch screen 616 overlaid on LCD display 614 or through a standard keyboard 618 supplemented by additional custom keys 620, such as an emergency VVI (EVVI) key. The EVVI key sets the IMD 501 to a safe VVI mode with high pacing outputs. This ensures life-sustaining pacing operation in nearly all situations but by no means is it desirable to leave cardiac stimulation device 100 in the EVVI mode at all times.

Typically, the physician initially controls the external device 502 to retrieve data stored within the implanted medical device and to also retrieve ECG data from ECG leads coupled to the patient's myocardium. To this end, CPU 602 transmits appropriate signals to a telemetry circuit 622, which provides components for directly interfacing with IMD 501. The telemetry subsystem 622 can include its own separate CPU 624 for coordinating the operations of the telemetry subsystem 622. The main CPU 602 of the external device 502 communicates with telemetry subsystem CPU 624 via internal bus 604. The telemetry subsystem 622 additionally includes a telemetry circuit 626 connected to a telemetry wand 628, which cooperate to receive and transmit signals electromagnetically from telemetry circuit 564 of the IMD 501. The telemetry wand 628 is placed over the chest of the patient near the IMD 501 to permit reliable transmission of data, over telemetric link 503, between the telemetry wand and the IMD 501. Typically, at the beginning of the programming session, the external programming device controls the IMD 501 via appropriate signals generated by telemetry wand 628 to output all previously recorded patient and device diagnostic information. Patient diagnostic information includes, for example, measured physiological variables data, recorded IEGM data and statistical patient data such as the percentage of paced versus sensed heartbeats. Device diagnostic data includes, for example, information representative of the operation of the IMD 501 such as lead impedances, battery voltages, battery Recommended Replacement Time (RRT) information and the like. Data retrieved from the IMD 501 is stored by the external device 502 either within a Random Access Memory (RAM) 630, a hard drive 608, within a floppy diskette placed within a floppy drive 610, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

Patient and device diagnostic data stored within the IMD 501 can be transferred to the external device 502. Further, the IMD 501 can be instructed to perform an electrode algorithms of the present invention, details of which are provided above.

The external device 502 can also include a Network Interface Card ("NIC") 660 to permit transmission of data to and from other computer systems via a router 662 and Wide Area Network ("WAN") 664. Alternatively, the external device 502 might include a modem for communication via the Public Switched Telephone Network (PSTN). Depending upon the implementation, the modem may be connected directly to internal bus 604 and may be connected to the internal bus via either a parallel port 640 or a serial port 642. Data transmitted from other computer systems may include, for example, data regarding medication prescribed, administered, or sold to the patient.

The CPU 602 can include an arrhythmia discrimination module 650 that can control the performance of the steps described above with reference to FIGS. 4A-4C, or subsets thereof, and/or can instruct the IMD 501 to perform certain such steps.

The external device 502 receives data from the IMD 501, including parameters representative of the current programming state of the IMD 501. The external device 502 can also receive IEGMs, samples thereof, and/or date indicative thereof from the IMD 501. Under the control of the physician, external device 502 displays the current programming parameters and permits the physician to reprogram the parameters. To this end, the physician enters appropriate commands via any of the aforementioned input devices and, under control of the CPU 602, the programming commands are converted to specific programming parameters for transmission to the IMD 501 via the telemetry wand 628 to thereby reprogram the IMD 501. Prior to reprogramming specific parameters, the physician may control the external programmer to display any or all of the data retrieved from the IMD 501, including displays of ECGs, displays of electrodes that are candidates as cathodes and/or anodes, and statistical patient information. Any or all of the information displayed by external device 502 may also be printed using a printer 636.

A speaker 644 is included for providing audible tones to the user, such as a warning beep in the event improper input is provided by the physician. Telemetry subsystem 622 may additionally include an input/output circuit 646 which can control the transmission of analog output signals, such as ECG signals output to an ECG machine or chart recorder. Other peripheral devices may be connected to the external device 502 via parallel port 640 or a serial port 642 as well. Although one of each is shown, a plurality of Input Output (IO) ports might be provided.

With the external device 502 configured as shown, a physician or other authorized user can retrieve, process, and display a wide range of information received from the IMD 501 and reprogram the IMD 501, including configurations of CRT pacing parameters, if needed. The descriptions provided herein with respect to FIG. 6 are intended merely to provide an overview of the operation of the example external device 502 and are not intended to describe in detail every feature of the hardware and software of the device and are not intended to provide an exhaustive list of the functions performed by the device.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 4A, 4B, and 4C. For another example, it is possible to change the boundaries of some of the blocks shown in FIGS. 5 and 6.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A device, comprising:
   one or more electrodes;
   a sensing circuit coupled to the one or more electrodes and configured to obtain a signal indicative of electrical activity of a patient's heart; and
   at least one of a processor or controller configured to
      obtain an ordered list of R-R intervals within a window leading up to a detection of a potential arrhythmia episode, wherein each of the R-R intervals has a respective duration;
      determine, based on the ordered list of R-R intervals within the window, pairwise differences between pairs of the R-R intervals that are various different intervals apart, to thereby produce M sets of pairwise differences;
      for each set of pairwise intervals, of the M sets of pairwise intervals, determine a median of the set or an indicator of the median;
      determine a measure of a dominant repeated R-R interval pattern within the window by determining a minimum of the M medians or the M indicators of the medians;
      compare the measure of the dominant repeated R-R interval pattern to a pattern threshold; and
      determine that the detection of the potential arrhythmia episode does not correspond to an actual arrhythmia episode, when the measure of the dominant repeated R-R interval pattern is below the pattern threshold, and in response thereto, at least one of allow data corresponding to the potential arrhythmia episode to be overwritten or prevent the data corresponding to the potential arrhythmia episode from being transmitted to another device.

2. A device, comprising:
one or more electrodes;
a sensing circuit coupled to the one or more electrodes and configured to obtain a signal indicative of electrical activity of a patient's heart; and
at least one of a processor or controller configured to
obtain an ordered list of R-R intervals within a window leading up to a detection of a potential arrhythmia episode, wherein each of the R-R intervals has a respective duration;
determine an indicator of a median R-R interval difference between pairs of the R-R intervals within the window that are k intervals apart, for each of k=1 to M, where M is an integer that is at least 4, to thereby produce M indicators of the median R-R interval difference; and
identify a minimum of the M indicators of the median R-R interval difference;
compare the minimum of the M indicators of the median R-R interval difference to a threshold; and
determine that the detection of the potential arrhythmia episode does not correspond to an actual arrhythmia episode, when the minimum of the M indicators of the median R-R interval difference is below the threshold, and in response thereto, at least one of allow data corresponding to the potential arrhythmia episode to be overwritten or prevent the data corresponding to the potential arrhythmia episode from being transmitted to another device.

3. The device of claim 2, wherein the M indicators of the median R-R interval difference comprise M median percent difference values each of which is determined, by the at least one of the processor or controller, using the equation:

Median Percent Difference for $k$=MEDIAN($100*|RR(n)-RR(n+k)|/RR(n)$), for intervals n=1:N and interval separations k=1:M, where
$RR(n)$ is a $n^{th}$ R-R interval within the window,
$RR(n+k)$ is a $(n+k)^{th}$ R-R interval within the window,
$|RR(n)-RR(n+k)|$ is the absolute value of $RR(n)-RR(n+k)$, and
N is a total number of R-R intervals within the window.

4. The device of claim 2, further comprising a transceiver configured to wireless communicate with an external device, wherein:
the device comprises an implantable medical device (IMD) that is configured to at least one of save within memory of the IMD or transmit to an external device, data corresponding one or more arrhythmia episodes detected by the IMD, so that the data is available at a later time for further analysis; and
after the IMD determines that the detection of the potential arrhythmia episode does not correspond to an actual arrhythmia episode, the IMD at least one of allows the data corresponding to the potential arrhythmia episode that is saved within the memory of the IMD to be overwritten or prevents the data corresponding to the potential arrhythmia episode from being transmitted to an external device using the transceiver of the IMD.

5. The device of claim 2, wherein the device comprises one of the following:
a user wearable device;
an insertable cardiac monitor (ICM);
a cardiac pacemaker to which one or more leads is/are attached;
a leadless cardiac pacemaker (LCP); or
an implantable cardioverter defibrillator (ICD).

6. A method for improving arrhythmia episode detection specificity, the method comprising:
obtaining an ordered list of R-R intervals within a window leading up to a detection of a potential arrhythmia episode, wherein each of the R-R intervals has a respective duration;
determining, based on the ordered list of R-R intervals within the window, pairwise differences between pairs of the R-R intervals that are various different intervals apart, to thereby produce M sets of pairwise differences;
determining a median of the set or an indicator of the median, for each set of pairwise intervals of the M sets of pairwise intervals;
determining a measure of a dominant repeated R-R interval pattern within the window by determining a minimum of the M medians or the M indicators of the medians;
comparing the measure of the dominant repeated R-R interval pattern to a pattern threshold;
in response to the measure of the dominant repeated R-R interval pattern being below the pattern threshold, determining that the detection of the potential arrhythmia episode does not correspond to an actual arrhythmia episode; and
in response to determining that the detection of the potential arrhythmia episode does not correspond to an actual arrhythmia episode, at least one of allowing data corresponding to the potential arrhythmia episode to be overwritten or preventing the data corresponding to the potential arrhythmia episode from being transmitted to another device.

7. A method for use by a device, the method comprising:
obtaining an ordered list of R-R intervals within a window leading up to a detection of a potential arrhythmia episode, wherein each of the R-R intervals has a respective duration;
for each of k=1 to M, where M is an integer that is at least 4, determining an indicator of a median R-R interval difference between pairs of the R-R intervals within the window that are k intervals apart, to thereby produce M indicators of the median R-R interval difference;
identifying a minimum of the M indicators of the median R-R interval difference;
comparing the minimum of the M indicators of the median R-R interval difference to a threshold; and
determining that the detection of the potential arrhythmia episode does not correspond to an actual arrhythmia episode, when the minimum of the M indicators of the median R-R interval difference is below the threshold, and in response thereto, at least one of allowing data corresponding to the potential arrhythmia episode to be overwritten or preventing the data corresponding to the potential arrhythmia episode from being transmitted to another device.

8. The method of claim 7, wherein the M indicators of the median R-R interval difference that are determined comprise M median percent difference values each of which is determined using the equation:

Median Percent Difference for $k$=MEDIAN($100*|RR(n)-RR(n+k)|/RR(n)$), for intervals n=1:N and interval separations k=1:M,
where
RR(n) is a $n^{th}$ R-R interval within the window,
RR(n+k) is a $(n+k)^{th}$ R-R interval within the window,
|RR(n)−RR(n+k)| is the absolute value of RR(n)−RR(n+k), and
N is a total number of R-R intervals within the window.

9. The method of claim 7, wherein:
the device that the method is for use by comprises an implantable medical device (IMD) that is configured to at least one of save within memory of the IMD or transmit to an external device, data corresponding one or more arrhythmia episodes detected by the IMD, so that the data is available at a later time for further analysis; and
after the IMD determines that the detection of the potential arrhythmia episode does not correspond to an actual arrhythmia episode, the IMD at least one of allows the data corresponding to the potential arrhythmia episode that is saved within the memory of the IMD to be overwritten or prevents the data corresponding to the potential arrhythmia episode from being transmitted by the IMD to an external device.

10. The method of claim 7, wherein the window comprises a specified period of time, and wherein the obtaining the ordered list of R-R intervals comprises:
obtaining an electrogram (EGM) or electrocardiogram (ECG) segment corresponding to the specified period of time leading up to the detection of the potential arrhythmia episode;
identifying R-waves within the EGM or ECG segment; and
determining intervals between consecutive ones of the R-waves.

11. A device, comprising:
one or more electrodes;
a sensing circuit coupled to the one or more electrodes and configured to obtain a signal indicative of electrical activity of a patient's heart; and
at least one of a processor or controller configured to
obtain an ordered list of R-R intervals within a window leading up to a detection of a potential arrhythmia episode, wherein each of the R-R intervals has a respective duration;
for a value for k, selected from a range of values for k,
determine a corresponding indicator of a median R-R interval difference between pairs of the R-R intervals within the window that are k intervals apart;
compare the indicator of the median R-R interval difference to a threshold; and
determine that the detection of the potential arrhythmia episode does not correspond to an actual arrhythmia episode, when the indicator of the median R-R interval difference is less than the threshold; and
the at least one of the processor or controller further configured to at least one of allow data corresponding to the potential arrhythmia episode to be overwritten, or prevent the data corresponding to the potential arrhythmia episode from being transmitted to another device, when it is determined that the detection of the potential arrhythmia episode does not correspond to an actual arrhythmia episode.

12. The device of claim 11, wherein when for a value of k, the at least one of a processor or controller determines that the detection of the potential arrhythmia episode does not correspond to an actual arrhythmia episode, then an indicator of the median R-R interval is determined for one or more further values for k within the range of values, until there is a determination that the detection of the potential arrhythmia episode does not correspond to an actual arrhythmia episode, or until there are no additional values to select for k within the range of values for k.

13. The device of claim 11, wherein the range of values for k is from 1 to M, where M is an integer that is at least 4, and wherein the at least one of the processor or controller is configured so that:
an initial value for k, that is selected from the range of values for k, is 1, and each time there is another selected value of k, the other selected value of k is produced by incrementing k so that k=k+1; or
an initial value for k, that is selected from the range of values for k, is M, and each time there is another selected value of k, the other selected value of k is produced by decrementing k so that k=k−1.

14. The device of claim 13, wherein the corresponding indicator of the median R-R interval difference between pairs of the R-R intervals, determined for a value of k, comprises a median percent difference value determined using the equation:

Median Percent Difference=MEDIAN(100*|RR(n)−RR(n+k)|/RR(n)), for intervals n=1:N, where
RR(n) is a $n^{th}$ R-R interval within the window,
RR(n+k) is a $(n+k)^{th}$ R-R interval within the window,
|RR(n)−RR(n+k)| is the absolute value of RR(n)−RR(n+k), and
N is a total number of R-R intervals within the window.

15. The device of claim 11, further comprising a transceiver configured to wireless communicate with an external device, wherein:
the device comprises an implantable medical device (IMD) that is configured to at least one of save within memory of the IMD or transmit to an external device, data corresponding one or more arrhythmia episodes detected by the IMD, so that the data is available at a later time for further analysis; and
after the IMD determines that the detection of the arrhythmia episode does not correspond to an actual arrhythmia episode, the IMD at least one of allows the data corresponding to the potential arrhythmia episode that is saved within the memory of the IMD to be overwritten or prevents the data corresponding to the potential arrhythmia episode from being transmitted to an external device using the transceiver of the IMD.

16. A method for use by a device, the method comprising:
(a) obtaining an ordered list of R-R intervals within a window leading up to a detection of a potential arrhythmia episode, wherein each of the R-R intervals has a respective duration;
(b) for a value for k, selected from a range of values for k,
(b.1) determining a corresponding indicator of a median R-R interval difference between pairs of the R-R intervals within the window that are k intervals apart;
(b.2) comparing the indicator of the median R-R interval difference to a threshold; and
(b.3) when the indicator of the median R-R interval difference is less than the threshold, then determining that the detection of the potential arrhythmia episode does not correspond to an actual arrhythmia episode; and (b.4) when the indicator of the median R-R interval difference is not less than the threshold, then repeating steps (b.1) through (b.3) for another selected value of k, until there is a determination that the detection of the potential arrythmia episode does not correspond to an actual arrhythmia episode, or until there are no additional values to select for k within the range of values for k; and (c) at least one of allowing data corresponding to the potential arrhythmia episode to be overwritten, or preventing the data corresponding to the potential arrhythmia episode from being transmitted to another device, when there is the determination that the detection of the potential arrhythmia episode does not correspond to an actual arrhythmia episode.

17. The method of claim 16, wherein the range of values for k is from 1 to M, where M is an integer that is at least 4, and wherein:
an initial value for k, that is selected from the range of values for k, is 1, and each time steps (b.1) through (b.3) are repeated for another selected value of k, the other selected value of k is produced by incrementing k so that k=k+1; or
an initial value for k, that is selected from the range of values for k, is M, and each time steps (b.1) through (b.3) are repeated for another selected value of k, the other selected value of k is produced by decrementing k so that k=k−1.

18. The method of claim 16, wherein the corresponding indicator of the median R-R interval difference between pairs of the R-R intervals, determined for a value of k, comprises a median percent difference value determined using the equation:

$$\text{Median Percent Difference} = \text{MEDIAN}(100 * |RR(n) - RR(n+k)| / RR(n)), \text{ for intervals } n = 1:N,$$

where
$RR(n)$ is a $n^{th}$ R-R interval within the window,
$RR(n+k)$ is a $(n+k)^{th}$ R-R interval within the window,
$|RR(n)-RR(n+k)|$ is the absolute value of $RR(n)-RR(n+k)$, and
N is a total number of R-R intervals within the window.

19. The method of claim 16, wherein:
the device that the method is for use by comprises an implantable medical device (IMD) that is configured to at least one of save within memory of the IMD or upload to an external device, data corresponding one or more arrhythmia episodes detected by the IMD, so that the data is available at a later time for further analysis;
steps (a) through (d) are performed by the IMD in response to the IMD detecting the potential arrhythmia episode; and
after the IMD determines that the detection of the potential arrhythmia episode does not correspond to an actual arrhythmia episode, the IMD at least one of allows the data corresponding to the potential arrhythmia episode that is saved within the memory of the IMD to be overwritten or prevents the data corresponding to the potential arrhythmia episode from being transmitted by the IMD to an external device.

20. The method of claim 16, wherein the window comprises a specified period of time, and wherein the (a) obtaining the ordered list of R-R intervals comprises:
obtaining an electrogram (EGM) or electrocardiogram (ECG) segment corresponding to the specified period of time leading up to the detection of the potential arrhythmia episode;
identifying R-waves within the EGM or ECG segment; and
determining intervals between consecutive ones of the R-waves.

* * * * *